(12) United States Patent
Yang et al.

(10) Patent No.: US 7,751,048 B2
(45) Date of Patent: *Jul. 6, 2010

(54) OPTOFLUIDIC MICROSCOPE DEVICE

(75) Inventors: Changhuei Yang, Pasadena, CA (US);
Demetri Psaltis, St. Sulpice (CH)

(73) Assignee: California Institute of Technology,
Pasadena, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 11/686,095

(22) Filed: Mar. 14, 2007

(65) Prior Publication Data

US 2007/0207061 A1    Sep. 6, 2007

Related U.S. Application Data

(63) Continuation-in-part of application No. 11/125,718, filed on May 9, 2005.

(60) Provisional application No. 60/590,768, filed on Jul. 23, 2004, provisional application No. 60/577,433, filed on Jun. 4, 2004, provisional application No. 60/783,920, filed on Mar. 20, 2006.

(51) Int. Cl.
*G01N 21/00* (2006.01)
(52) U.S. Cl. .................. 356/436; 356/440; 435/288.7
(58) Field of Classification Search ................. 385/129; 435/288.7; 356/432
See application file for complete search history.

(56) References Cited

U.S. PATENT DOCUMENTS 5,362,653 A * 11/1994 Carr et al. .................. 436/165
6,499,499 B2 * 12/2002 Dantsker et al. ................ 137/1
7,045,781 B2 * 5/2006 Adamec et al. ............. 250/310
7,271,885 B2 * 9/2007 Schermer .................... 356/134
2003/0142291 A1 * 7/2003 Padmanabhan et al. ....... 356/39
2003/0174992 A1   9/2003 Levene et al.
2003/0203502 A1  10/2003 Zenhausern et al.
2004/0156610 A1 * 8/2004 Charlton et al. ............. 385/129
2006/0003145 A1 * 1/2006 Hansen et al. .............. 428/131

OTHER PUBLICATIONS

Adams, Mark L. et al.; "Microfluidic integration on detector arrays for absorption and fluorescence micro-spectrometers"; 2003, *Sensors and Actuators A*, vol. 104, pp. 25-31.
Beebe, David J. et al.; "Physics and Applications of Microfluidics in Biology", 2002, *Annu. Rev. Biomed. Eng.*, vol. 4, pp. 261-286.

(Continued)

*Primary Examiner*—Tarifur Chowdhury
*Assistant Examiner*—Tara S Pajoohi
(74) *Attorney, Agent, or Firm*—Sheila Martinez-Lemke

(57) ABSTRACT

Optofluidic microscope devices and methods of using optofluidic microscope devices, where each optofluidic device comprises a body with a fluid channel having a surface, light transmissive regions in the body wherein the light transmissive regions have different dimensions, an illumination source adapted to provide illumination through the light transmissive regions, and an optical detector adapted to receive light from the illumination source through the light transmissive regions. The light transmissive regions and optical detector can be used to image an object flowing through the fluid channel.

23 Claims, 19 Drawing Sheets

OTHER PUBLICATIONS

Bethe, H.A.; "Theory of Diffraction by Small Holes"; 1944, *The Physical Review*. vol. 66, Nos. 7-8, pp. 163-182.

Biddiss, Elaine et al.; "Heterogeneous Surface Charge Enhanced Micromixing for Electrokinetic Flows"; 2004, *Anal. Chem.*, vol. 76, pp. 3208-3213.

Boppart, S.A. et al.; "Forward-imaging instruments for optical coherence tomography"; 1997, *Optics Letters*, vol. 22, pp. 1618-1620.

Cao, Jinhua at al.; "Brownian Particle Distribution in Tube Flows"; 2004, *Proceedings of IMECE04*, vol. 260, pp. 243-252.

Cheng, Ya et al.; "Microfluidic laser embedded in glass by three-dimensional femtosecond laser microprocessing"; 2004, *Optics Letters*, vol. 29, No. 17, pp. 2007-2009.

Chronis, Nikolas et al.; "Total internal reflection-based biochip utilizing a polymer-filled cavity with a micromirror sidewall"; 2004, *Lab Chip*, vol. 4, pp. 125-130.

Courjon, Daniel; "Near-field microscopy and near-field optics"; 2003, *Imperial College Press*, 317 pages.

Dahan, M. et al.; "Time-gated biological imaging by use of collidal quantum dots"; 2001, *Optics Letters*, vol. 26, No. 11, pp. 825-827.

de Abajo, F.J. Garcia; "Light transmission through a single cylindrical hole in a metallic film"; 2002, *Optics Letters*, vol. 10, No. 25, pp. 1475-1464.

de Fornel, F.; "Evanescent waves from Newtonian optics and Atomic optics"; 2001,*Springer*. 270 pages.

Heng, Xin et al.; "Optofluidic Microscopy"; 2005, *Proceedings of the ICMM2005 3rd International Conference on Microchannels and Minichannels*: pp. 1-6.

Jaiswal, Jyoti K. et al.; "Long-term multiple color imaging of live cells using quantum dot bioconjugates"; 2003, *Nature Biotechnology*, vol. 21, pp. 47-51.

Nott, Prabhu R. et al.; "Pressure-driven flow of suspensions: simulation and theory"; 1994, *J. Fluid Mech.*, vol. 275, pp. 157-199.

Segre, G. et al.; "Behavior of macroscopic rigid spheres in Poiseuille flow: Part 1. Determination of local concentration by statistical analysis of particle passages through crossed light beams"; 1962, *J. Fluid Mech.*, vol. 14, pp. 115-135.

Segre, G. at al.; "Behavior of macroscopic rigid spheres in Poiseuille flow: Part 2. Experimental results and interpretation"; 1982, *J. Fluid Mech.*, vol. 14, pp. 136-157.

Seo, Jeonggi et al.; "Disposable Integrated microfluidics with self-aligned planar microlenses"; 2004, *Sensors and Actuators B*, vol. 99, pp. 615-622.

Stone, H.A. et al.; "Engineering Flows in Small Devices: Microfluidics Toward a Lab-on-a-Chip"; 2004, *Annu. Rev. Fluid Mech.*, vol. 36, pp. 381-411.

Tearney, G.J. et al.; "Scanning single-mode fiber optic catheter-endoscope for optical coherence tomography"; 1996, *Optics Letters*, vol. 21, pp. 543-545.

Thorsen, Todd et al.; "Microfluidic Large-Scale Integration"; 2002, *Science*. vol. 298, pp. 580-584.

\* cited by examiner

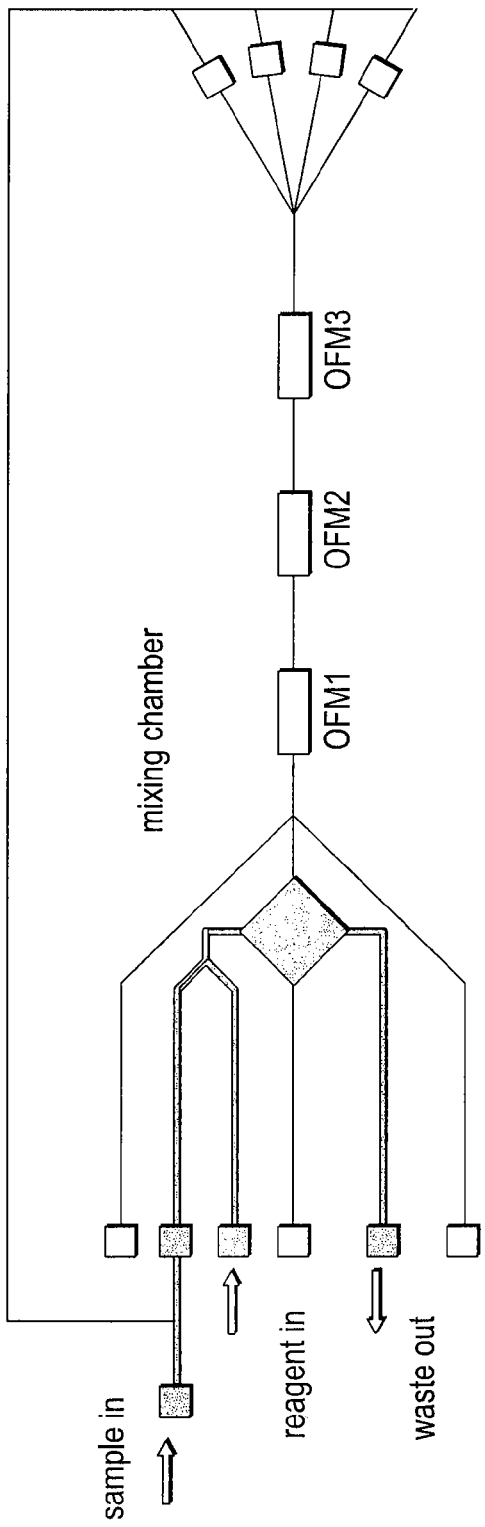
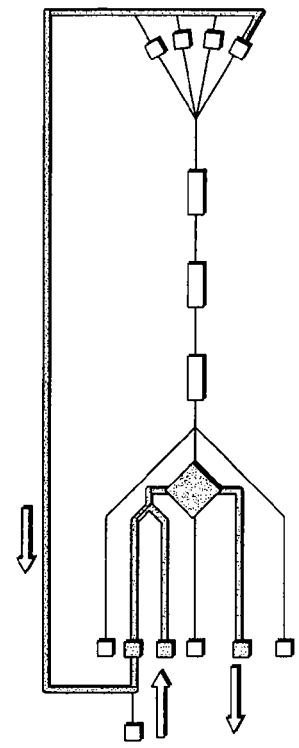
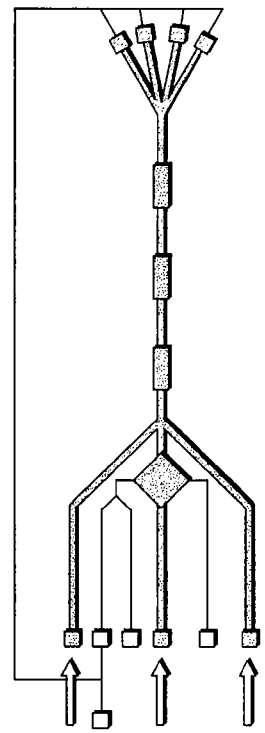
FIG. 9(a)
FIG. 9(b)
FIG. 9(c)

OPTOFLUIDIC MICROSCOPE DEVICE

CROSS-REFERENCES TO RELATED APPLICATIONS

This application is a continuation-in-part application of U.S. patent application Ser. No. 11/125,718, filed on May 9, 2005, which is a non-provisional of and claims priority to U.S. provisional patent application Nos. 60/590,768, filed on Jul. 23, 2004, and 60/577,433, filed on Jun. 4, 2004. This application is also a non-provisional of, and claims the benefit of the filing date of U.S. provisional patent application No. 60/783,920, filed on Mar. 20, 2006. All of these applications are herein incorporated by reference in their entirety for all purposes.

STATEMENT AS TO RIGHTS TO INVENTIONS MADE UNDER FEDERALLY SPONSORED RESEARCH OR DEVELOPMENT

Not Applicable

BACKGROUND OF THE INVENTION

The field of microfluidics has advanced rapidly. These advancements relate to the development of large-scale integration of microfluidic circuits, and numerous applications of microfluidics to life science research. Currently, optical microscopy is employed in microfluidic research as a technique to study fundamental microscale flow physics as well as biological targets. It is also used to study processes that are performed within these integrated microfluidic systems. In general, these devices rely on a macro-scale infrastructure (e.g. bulk microscopes, chip readers) to analyze biological targets.

Near field scanning optical microscopes (NSOMs) are extensively used to study biological targets. NSOMs can optically resolve structures with spatial resolutions of ~50 nm. An NSOM uses a strongly enhanced and tightly confined optical field at the end of an NSOM probe tip to optically probe a specific location on a target sample. NSOMs are especially useful for profiling bacteria, because bacteria cannot be easily imaged with conventional optical microscopy. In comparison to other high resolution imaging devices, such as scanning electron microscopes, NSOMs are able to selectively map the distribution of proteins or biochemicals in samples via fluorescence. In addition, NSOM imaging methods are non-destructive and can be used to image bioentities that are immersed in buffer media. Given all these advantages, one would expect that NSOMs would be widely used in clinical applications to distinguish bacteria types. However, the lack of publications on this suggests that significant technical barriers exist to using NSOMs. One such barrier is the difficulty of performing high throughput imaging with an NSOM. High throughput imaging requires raster scanning the probe tip over a target bioentity.

Embodiments of the invention are directed to devices which are improvements over NSOMs and conventional microfluidic systems that use bulky optics.

SUMMARY OF THE INVENTION

Embodiments of the invention are directed to optofluidic microscope devices or OFM devices. The optofluidic microscope devices according to embodiments of the invention are able to achieve resolutions similar to those of NSOMs. However, unlike NSOMs, embodiments of the invention can be used for high throughput imaging.

One embodiment of the invention is directed to an optofluidic microscope device comprising: a body comprising a fluid channel having a surface; light transmissive regions with different dimensions in the body; an illumination source adapted to provide illumination through the light transmissive regions with different dimensions; and an optical detector adapted to receive light from the illumination source through the light transmissive regions.

Another embodiment of the invention is directed to an optofluidic microscope device comprising: a body comprising a fluid channel having surface; a plurality of discrete light emitting regions on or under the surface; and an optical detector adapted to receive light generated by the plurality of discrete light-emitting regions.

Another embodiment of the invention is directed to an optofluidic microscope device comprising: a body comprising a fluid channel having surface; at least one light imaging element on or under the surface; and an optical detector adapted to receive light generated by the at least one light imaging element.

The optofluidic microscope devices according to some embodiments of the invention can use off the shelf detectors such as CCDs (charge coupled devices). Based on the parameters of off-the-shelf linear CCD arrays, a 100×100 pixel image of a bacterium can be acquired by an optofluidic microscope device according to an embodiment of the invention within a time frame as short as 1 millisecond. In embodiments of the invention, numerous optofluidic microscope devices may also be operated in parallel on a single chip.

The high speed processing capability of embodiments of the invention and the ability to use multiple optofluidic microscope devices in embodiments of the invention allow embodiments of the invention to have substantially higher imaging throughput rates than NSOMs. For example, in an NSOM device, the acquisition time for a 100×100 pixel image is about 10 milliseconds. In comparison, a parallel series of 10 optofluidic microscope devices built on a single 1000 pixel linear CCD array can provide up to one hundred 100×100 pixel images in the time that an NSOM creates a single image. The high throughput imaging capability and high resolution of the optofluidic microscope devices according to embodiments of the invention make them highly suited for various clinical applications. Such applications include differentiating between different bacteria types.

Also, the optofluidic microscope devices according to embodiments of the invention eliminate the bulky optics (e.g., sets of objective lenses and complex microscope setups) that are used to obtain biological images in conventional microfluidic devices. Unlike conventional imaging systems, the optofluidic microscope devices according to embodiments of the invention are portable and compact.

Methods of making and methods of using the optofluidic microscope devices are also disclosed.

These and other embodiments of the invention are described in further detail below.

Figure 3A:
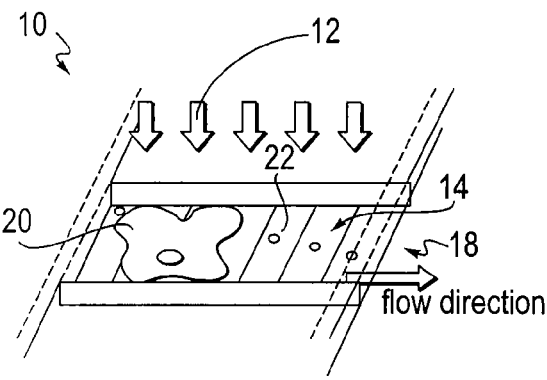

FIG. 3(a) is another schematic drawing of an optofluidic microscope device according to embodiment of the invention from a close up, perspective view.

Figure 3B:
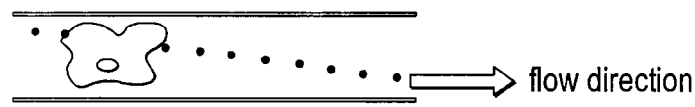

FIG. 3(b) is a schematic drawing of a top view of the fluid channel in the optofluidic microscope device shown in FIG. 3(a). The light transmissive regions in the bottom of the fluid channel form a line that is slanted with respect to its walls.

Figure 3C:
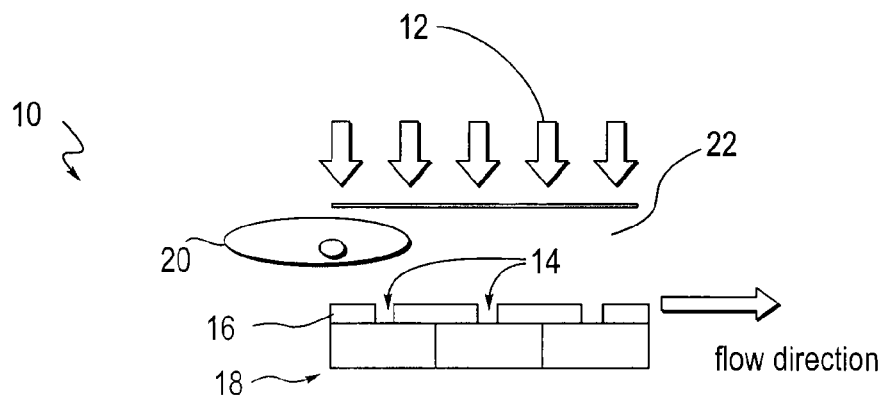

FIG. 3(c) is a schematic drawing of a side view of the optofluidic microscope device shown in FIG. 3(a).

Figure 3D:
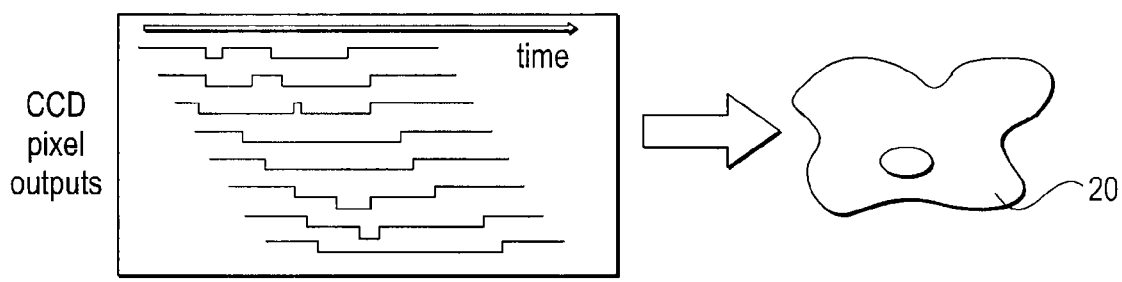

FIG. 3(d) shows collected time traces from each light detecting element in the optofluidic microscope device, wherein each light detecting element can produce an output that can be used to create an object image.

FIGS. 4(a)-4(e) show cross-sections of an optofluidic microscope device as it is being made.

Figure 5:
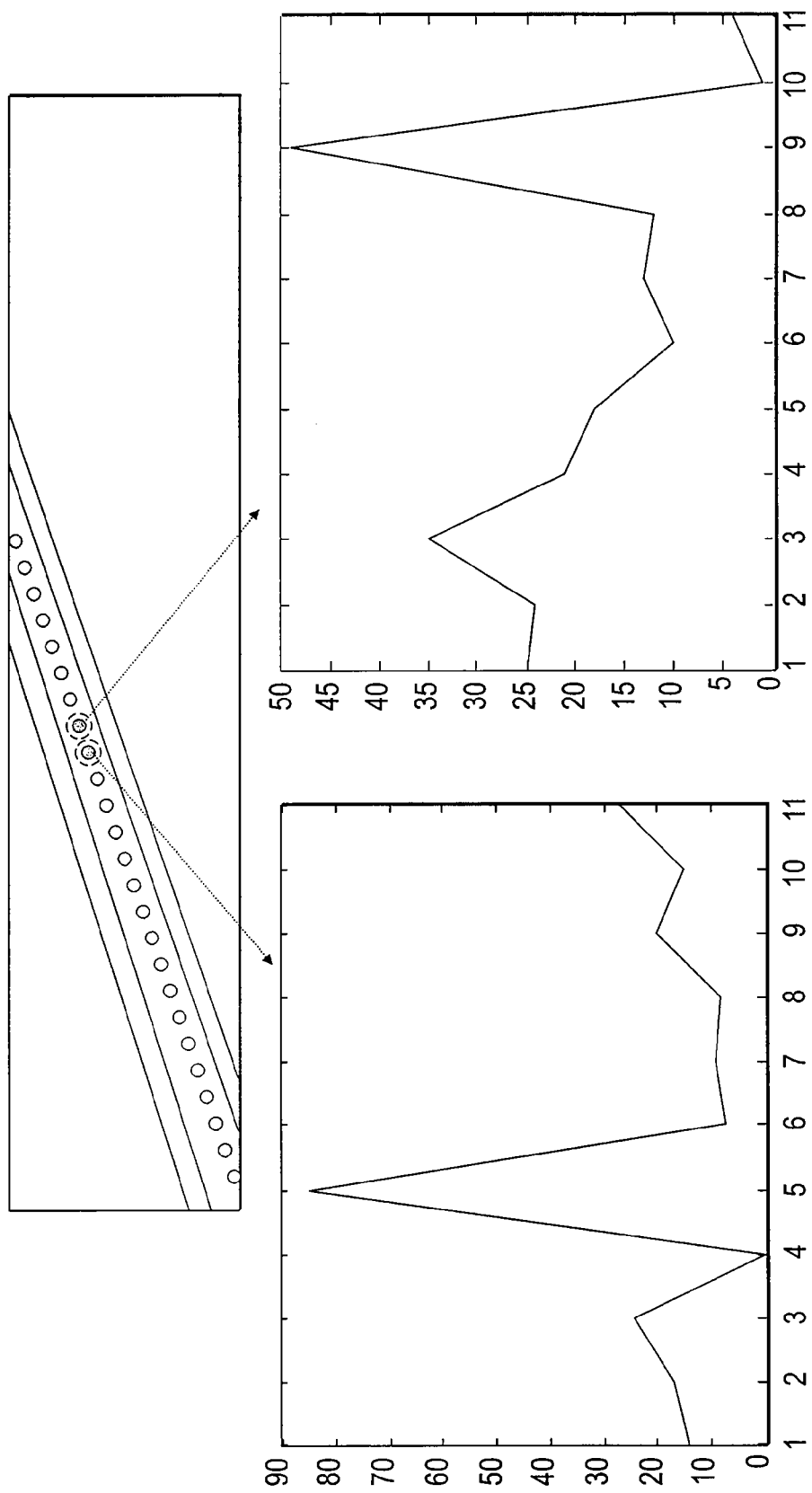

FIG. 5 shows a microscope image of an optofluidic microscope device and two graphs of transmission intensity vs. time. The left graph shows the change in transmission intensity through the left hole as indicated by a first corresponding arrow. The right graph shows the intensity change through the right hole as indicated by a second corresponding arrow.

Figure 6A:
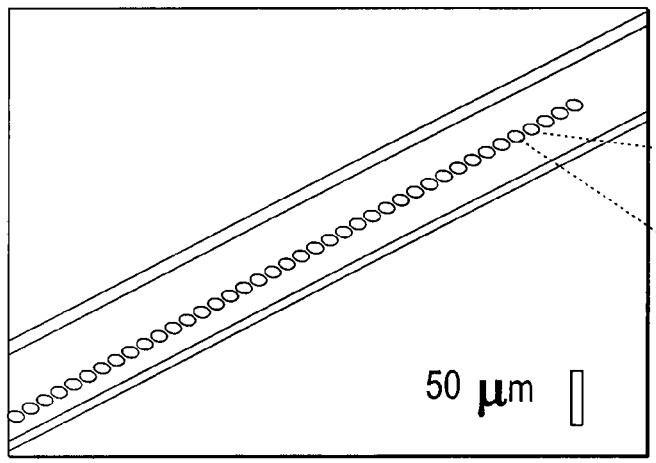

FIG. 6(a) shows a top view transmission image of an optofluidic microscope device. The light transmissive regions in the optofluidic microscope device are in the form of holes (about 0.5 microns in diameter).

FIG. 6(b) shows occlusion time traces through adjacent holes in an optofluidic microscope device according to an embodiment of the invention.

Figure 6:
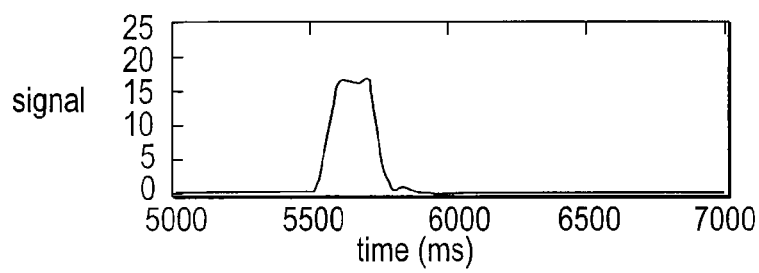
Figure 6:
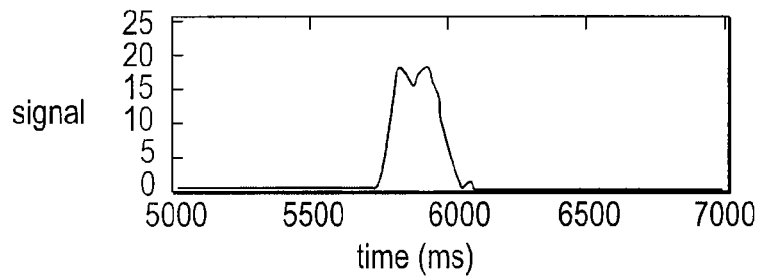
Figure 6C:
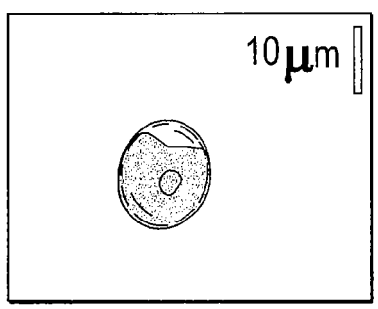

FIG. 6(c) shows a microscope image of a chlamoydomonas.

Figure 6D:
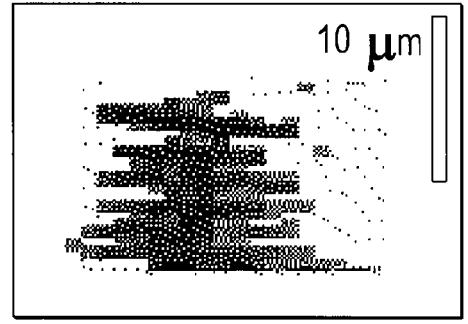

FIG. 6(d) shows preliminary data showing an optofluidic microscope device image of a chlamoydomonas.

Figure 7:
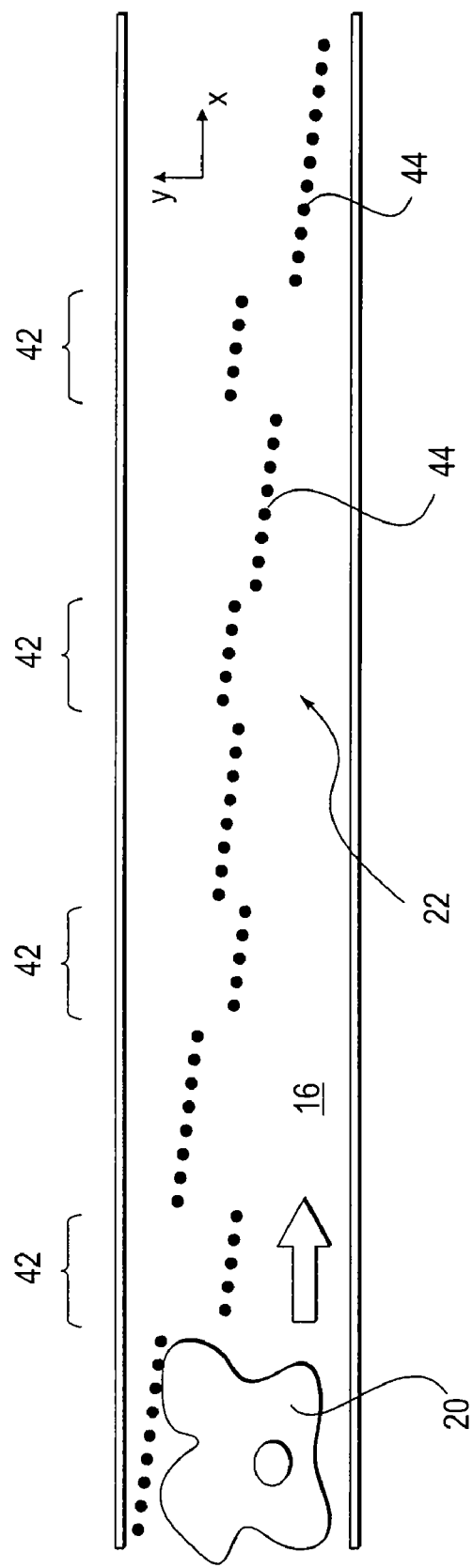

FIG. 7 shows interspersed reference hole array sets along the length of an optofluidic microscope device.

Figure 8:
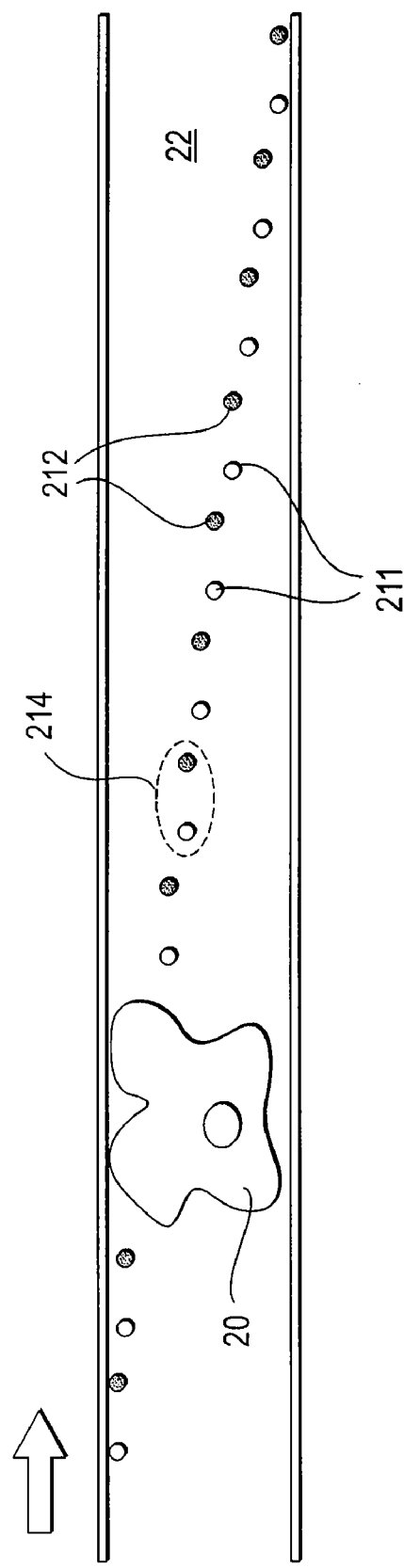

FIG. 8 shows another optofluidic microscope device according to an embodiment of the invention. In this embodiment, light transmissive regions with two different sizes are used in the optofluidic microscope device.

FIGS. 9(a)-9(c) show a schematic of system that uses optofluidic microscope devices. These Figures show a blood differential unit in various operational stages. Active elements are shown. FIG. 9(a) shows input and mixing where a sample is mixed with a reagent. FIG. 9(b) shows optofluidic microscope device measurements where a mixture is imaged through a series of optofluidic microscope devices with different transmission optical filters. FIG. 9(c) shows reprocessing, where any given fraction of an analyte may be re-mixed with a different reagent and then re-analyzed.

Figure 10A:
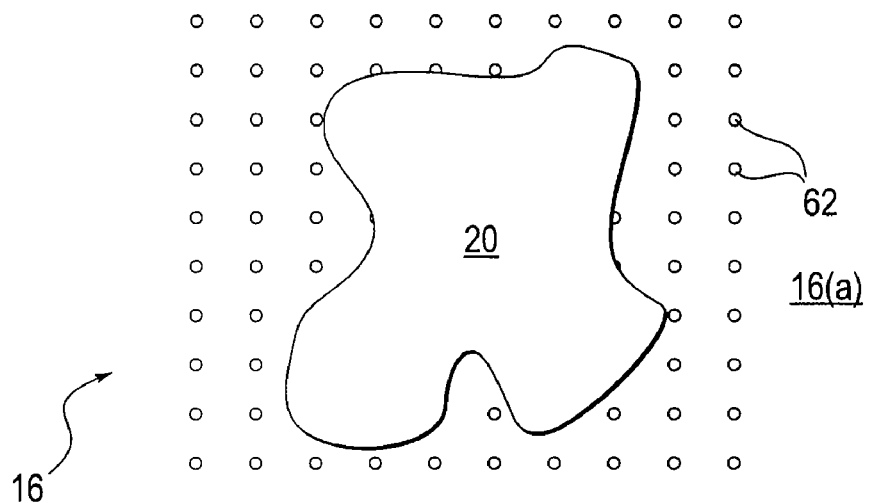

FIG. 10(a) shows a top plan view of another optofluidic microscope device according to an embodiment of the invention. In this embodiment, instead of holes in a fluid channel, distinct quantum dots are used to image a biological entity such as a cell.

Figure 10B:
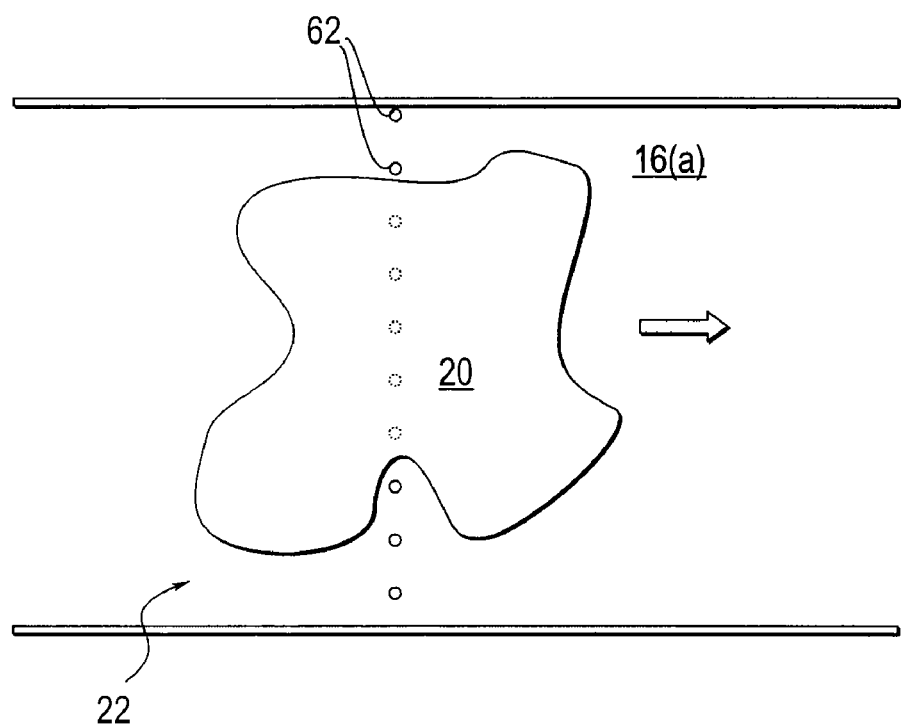

FIG. 10(b) shows another embodiment of an optofluidic microscope device according to an embodiment of the invention from a top view. The quantum dots are in a line, rather than in an array.

Figure 11A:
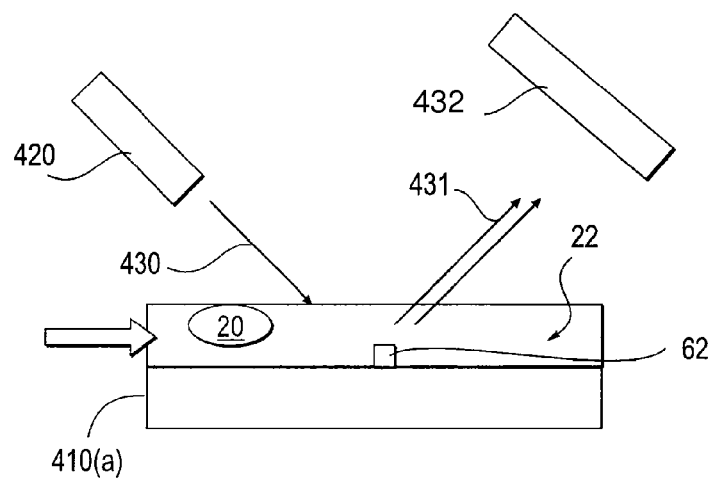
Figure 11B:
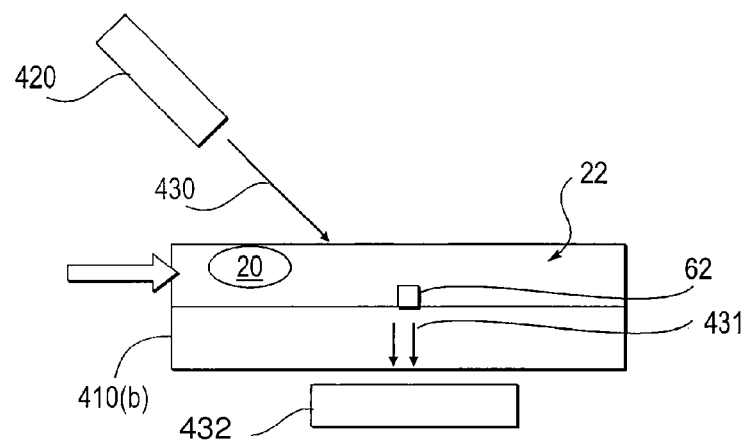

FIGS. 11(a) and 11(b) show exemplary illumination source and detector configurations for embodiments like those shown in FIGS. 10(a) and 10(b).

Figure 12:
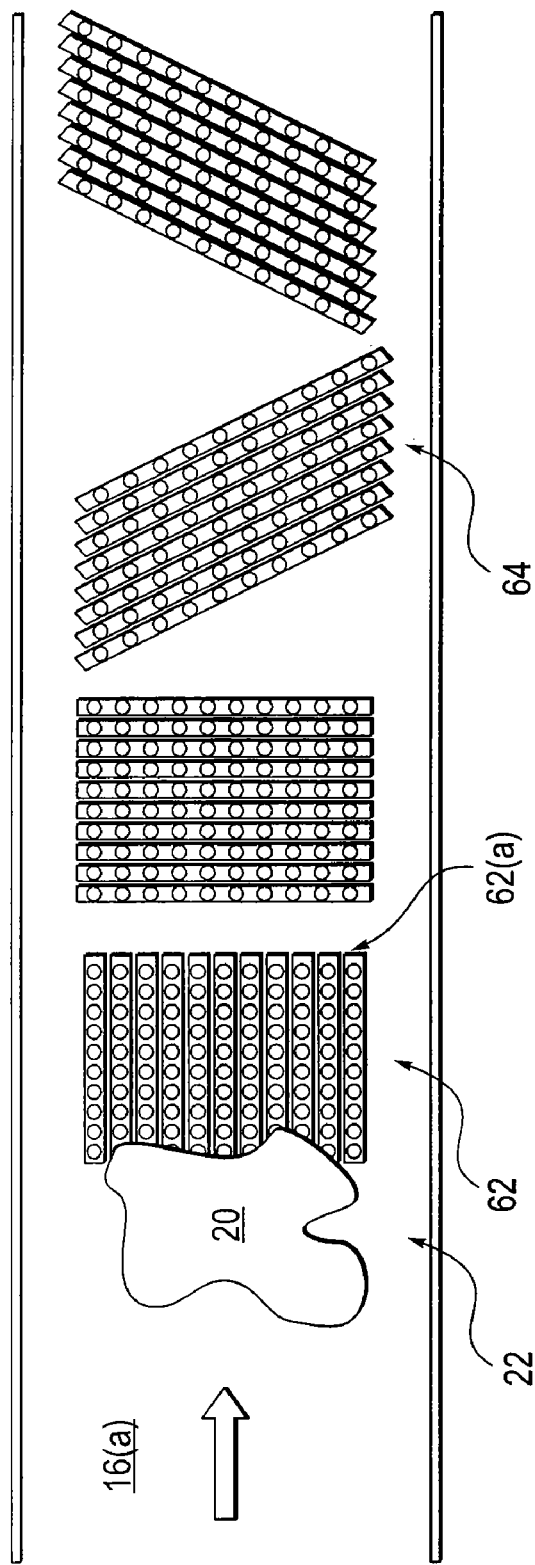

FIG. 12 shows a top view of another embodiment of the invention using quantum dots. In this embodiment, two dimensional arrays of quantum dots are in a fluid channel and they are oriented differently with respect to each other.

Figure 13:
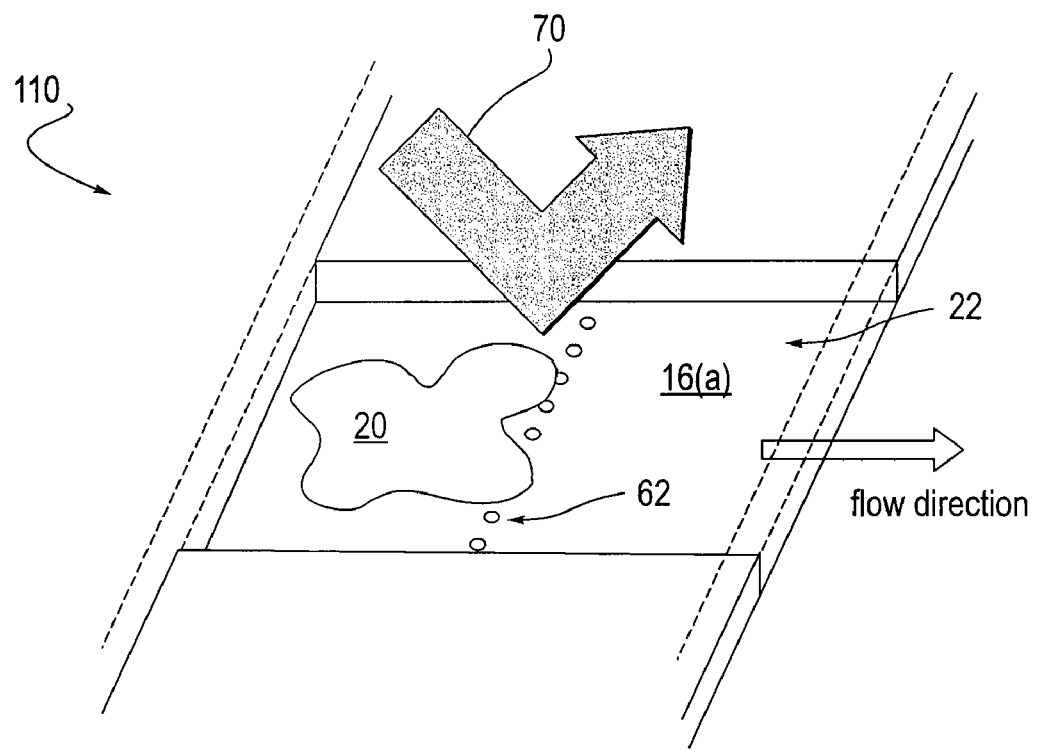
Figure 13:
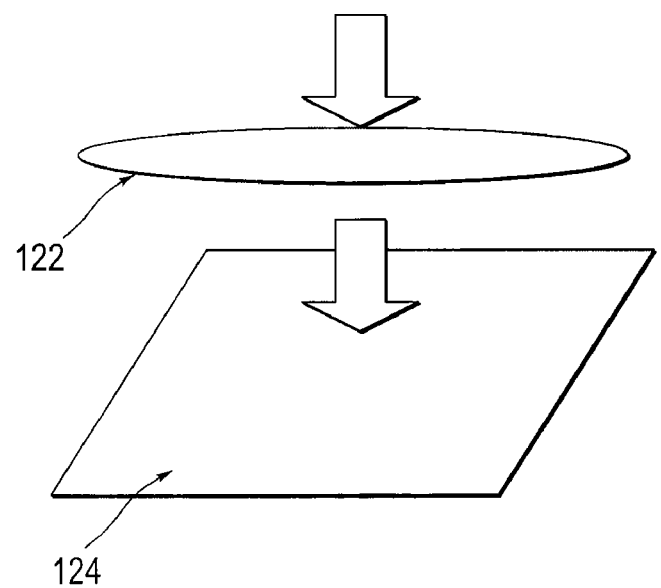

FIG. 13 shows a schematic perspective view of the optofluidic microscope device shown in FIG. 10(b).

Figure 14:
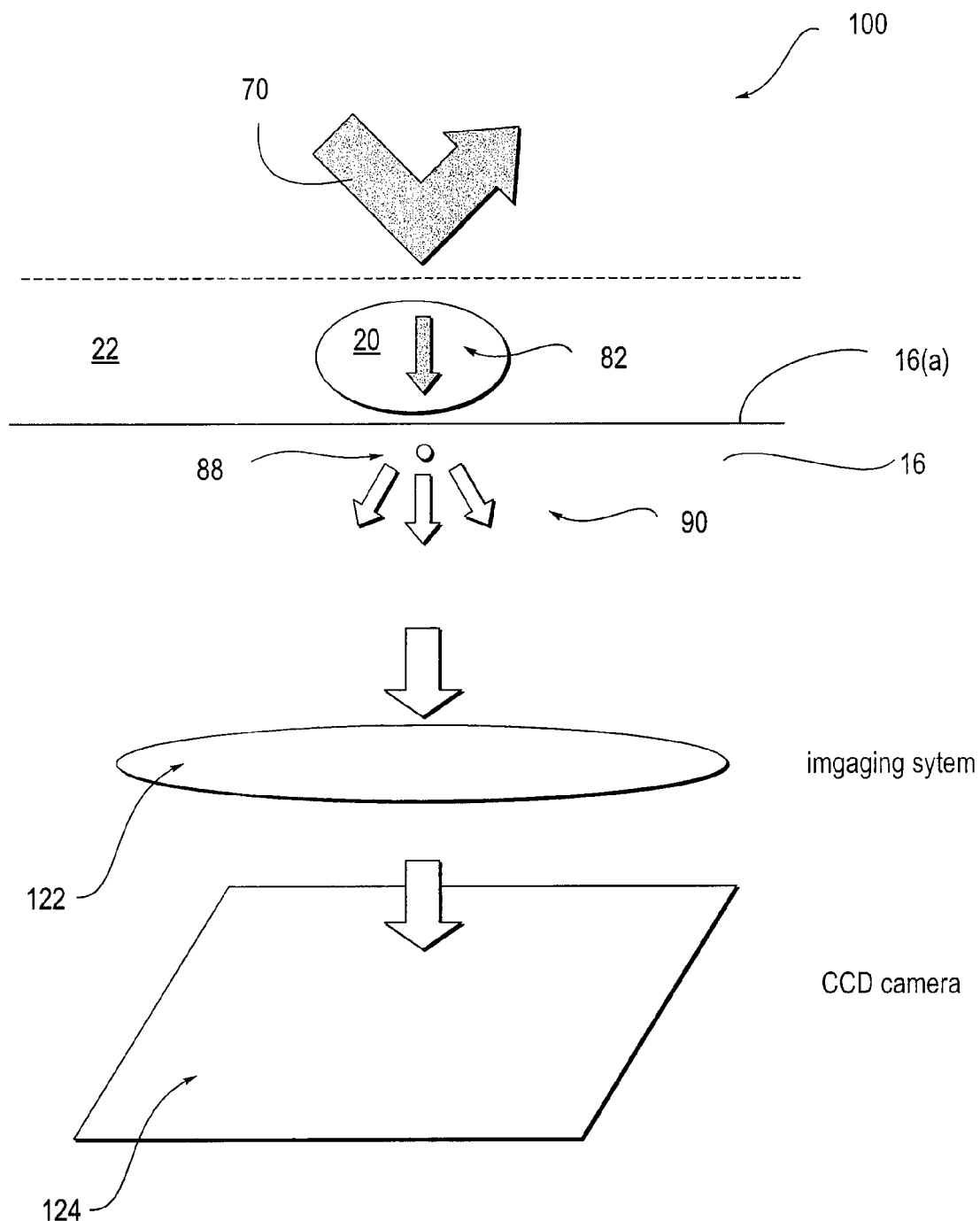

FIG. 14 shows a side view of an optofluidic microscope device using quantum dots.

Figure 15:
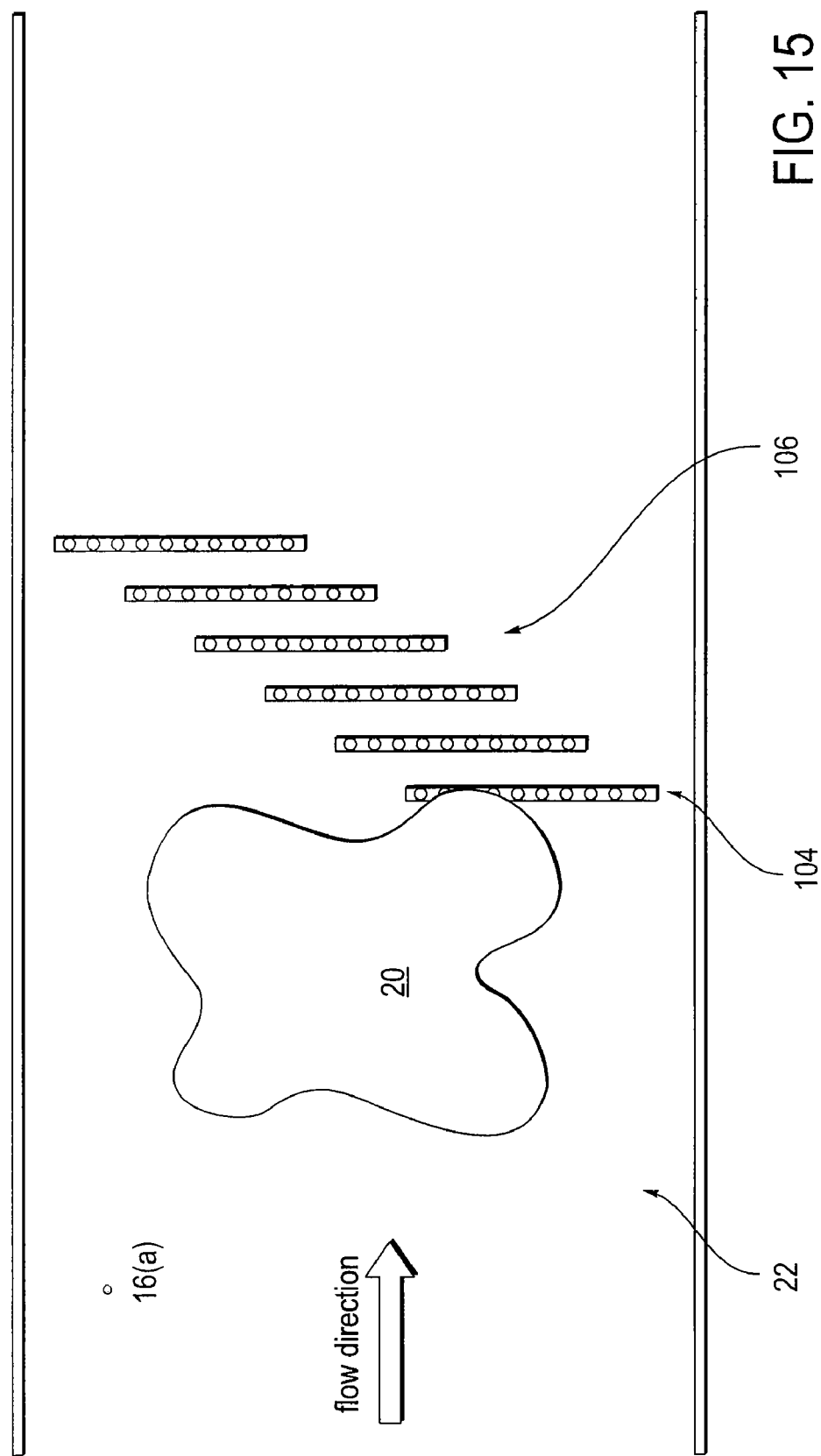

FIG. 15 shows a top view of another embodiment of the invention using quantum dots. In this embodiment, the quantum dots are arranged in lines and the lines are slanted with respect to each other.

Figure 16:
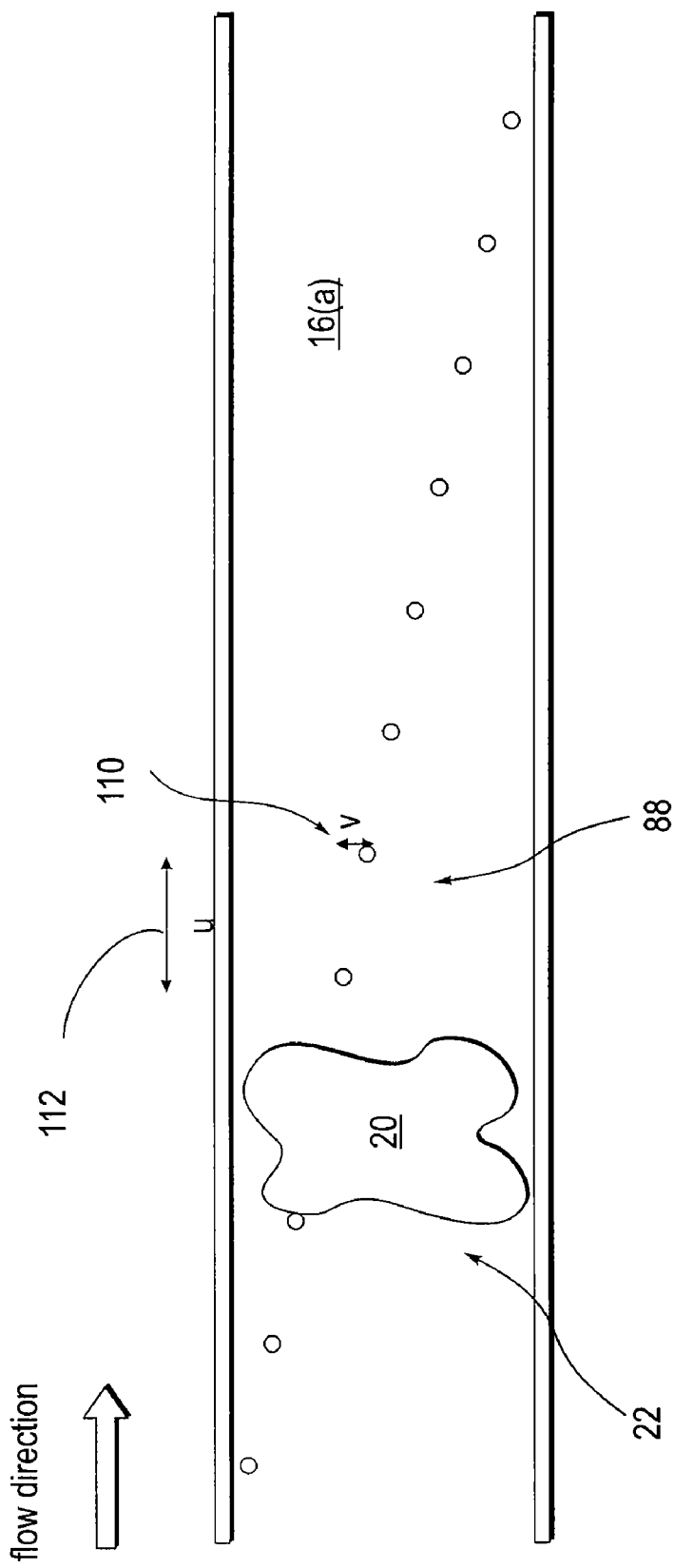

FIG. 16 shows a top view of another embodiment of the invention using quantum dots. The quantum dots in this embodiment are spaced apart by larger distances than prior embodiments.

Figure 17:
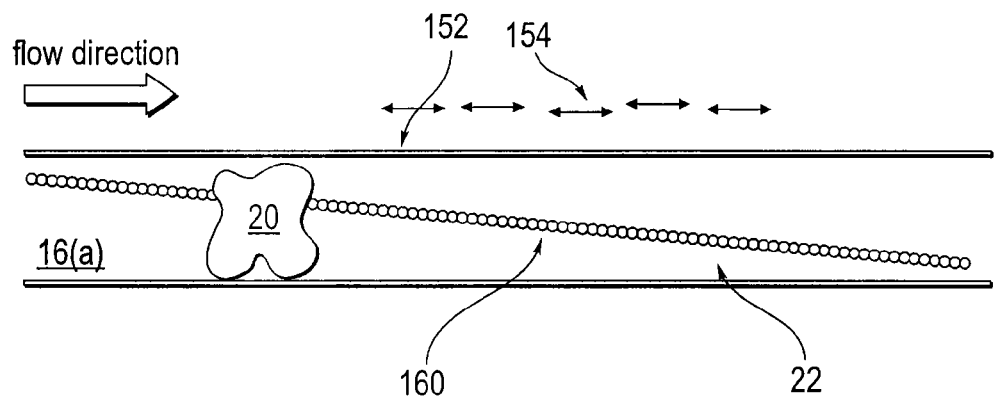

FIG. 17 shows a top view of another embodiment of the invention using quantum dots. The quantum dots in this example are in the form of diagonal lines.

Figure 18:
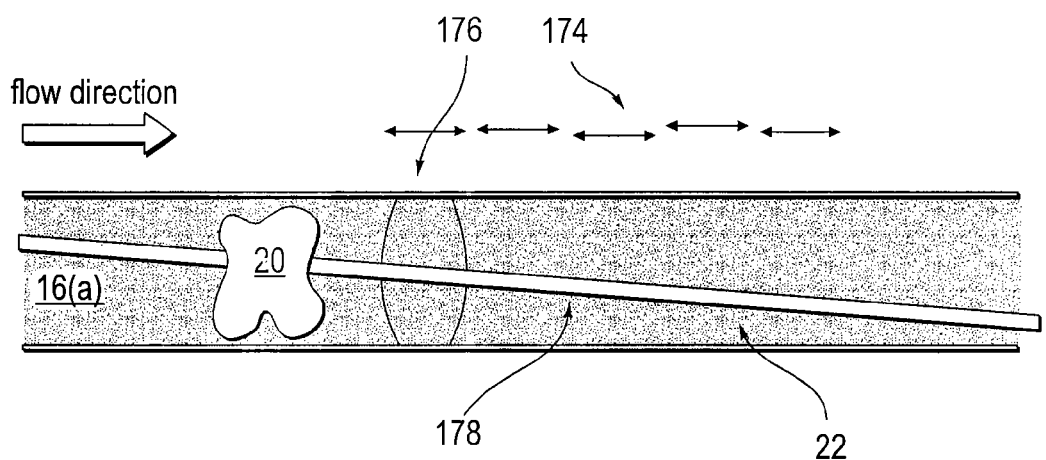

FIG. 18 shows an embodiment where a thin transparent or reflective trench structure is formed in a substrate.

Figure 19:
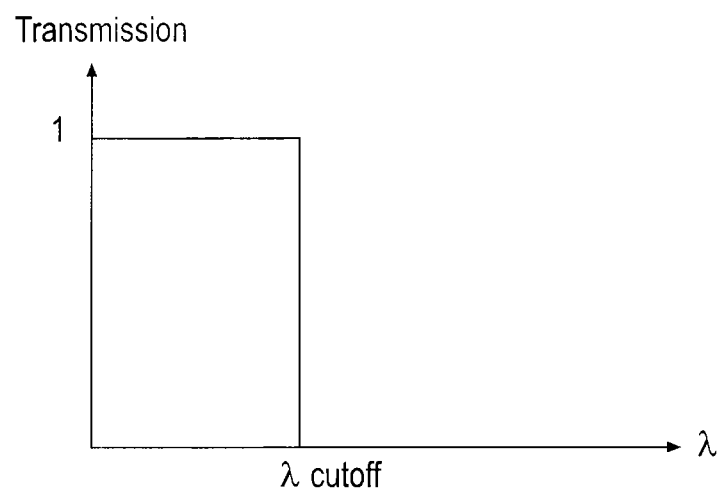

FIG. 19 shows an exemplary graph of light transmission vs. wavelength.

Figure 20A:
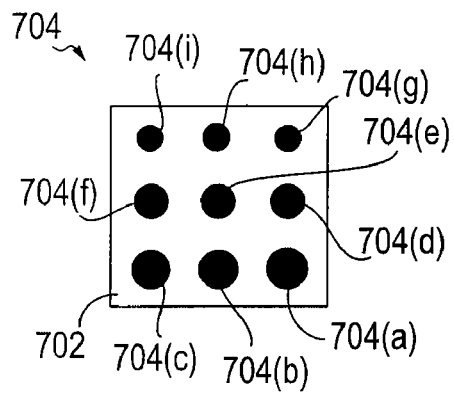

FIG. 20(a) shows a plan view of body including light transmissive regions, wherein the light transmissive regions comprise different sizes.

Figure 20B:
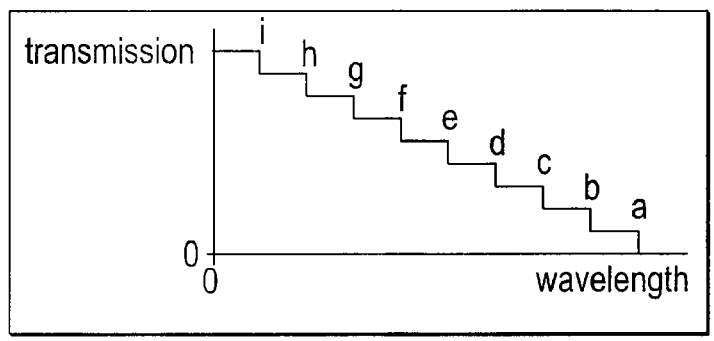

FIG. 20(b) shows a graph of transmission vs. wavelength.

Figure 20C:
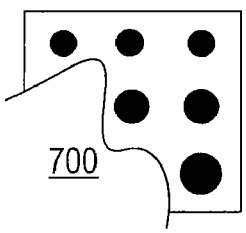

FIG. 20(c) shows a plan view of a body including light transmissive regions, wherein the light transmissive regions comprise different sizes, when an object blocks the light transmissive regions.

Figure 20D:
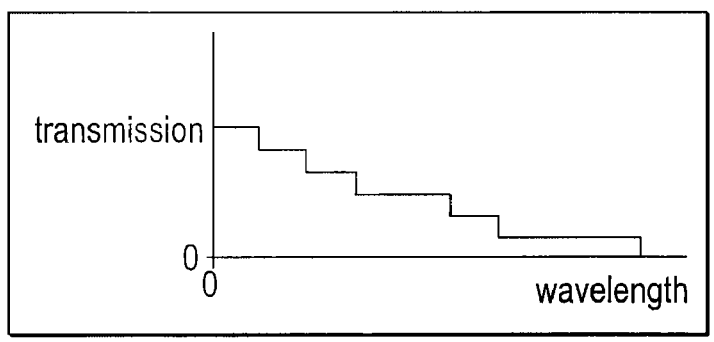

FIG. 20(d) shows another graph of transmission vs. wavelength when an object blocks some of the light transmissive regions with different sizes.

Figure 21:
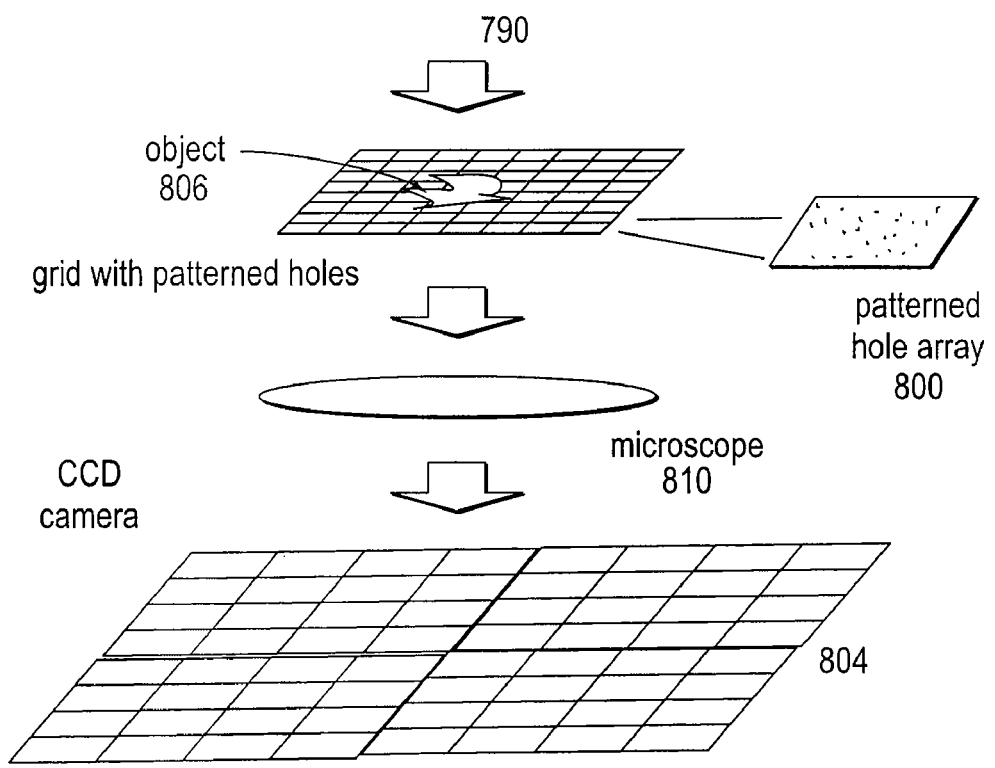

FIG. 21 shows a system according to an embodiment of the invention.

In the Figures, like numerals designate like elements.

DETAILED DESCRIPTION

Embodiments of the invention are directed to optofluidic microscopes that can use light transmissive regions (e.g., spaced holes) or discrete light emitting elements (e.g., quantum dots) in a body defining at least a portion of a fluid channel. The light transmissive regions or the light emitting elements (in conjunction with other elements) can be used to image entities such as biological entities passing through the fluidic channel. Other embodiments are directed to optofluidic microscope devices that have at least one light imaging element in or on a surface of a bottom wall defining a fluid channel. The light imaging elements may be in the form of one or more light transmissive regions such as holes, one or more light emitting elements such as quantum dots, one or more linear structures such as reflective lines or lines of closely adjacent quantum dots, or even one or more light scattering bodies such as nanoparticles.

In the specifically described embodiments, the imaging of cells is mentioned. It is understood, however, that embodiments of the invention are not limited thereto. For example, instead of cells, any suitable object can be imaged. The object can be a chemical or biological entity. Examples of biological entities include whole cells, cell components, microorganisms such as bacteria or viruses, cell components such as proteins, etc. Chemical entities such as macromolecules may also be imaged by embodiments of the invention.

I. Optical Devices Using Light Transmissive Regions

A. Exemplary Embodiments Using Light Transmissive Regions

One embodiment of the invention is directed to an optofluidic microscope device. The optofluidic microscope device comprises a body defining at least a portion of a fluid channel. Light transmissive regions are in the body, and the body may have a surface that coincides with the bottom surface of the fluid channel. An illumination source provides light which passes through the light transmissive regions and is received by an optical detector. The optical detector is disposed on the opposite side of the surface as the illumination source, and may have discrete individual light detecting elements (e.g., pixels) that are respectively associated with the light transmissive regions. The optofluidic microscope device is much more compact than conventional microfluidic optical systems.

In some embodiments, the light transmissive regions are micro-holes or nano-holes defined in an opaque or semi-opaque layer, which may form part of the body. The holes may be defined using any suitable hole formation process including electron beam lithography. In embodiments of the invention, each hole (or light transmissive region) may have a size (e.g., diameter) less than about 5, 1, or 0.5 microns. The holes may also have any suitable shape, and may be circular, square, etc.

The holes may also form an array. The array may be one or two dimensional. For example, in some embodiments, the holes in the array may form a slanted line extending from one lateral side of the fluid channel to the other lateral side of the fluid channel.

In some embodiments, the light transmissive regions in the array may have different sizes. By providing differently sized light transmissive regions, it is possible to monitor a light transmission spectrum to determine the shape of an object that is passing over the light transmissive regions.

In some embodiments, there may be at least about 2, 5, or 10 differently sized light transmissive regions in an array of light transmissive regions, and they may be arranged in the array in any suitable manner. Preferably, the dimensions (e.g., diameters) of the light transmissive regions may increase in some orderly manner (e.g., increasing dimensions within a row or within a column of light transmissive regions) in an array of light transmissive regions. For example, a row may have light transmissive regions incrementally increasing in size (e.g. from 0.1 to 1.0 microns in increments of 0.1 microns) and repeating the pattern.

Any suitable number or density of holes or light transmissive regions may be used in embodiments of the invention. For example, there may be greater than about 10, 50, 100, or even 1000 light transmissive regions per optofluidic microscope device. There may also be more than 10, 50, 100, or even 1000 light transmissive regions per square centimeter in some embodiments.

The light transmissive regions and the optical detector can form an "imager" in the optofluidic microscope device. The imager can image entities such as biological targets, which may be present in biological or non-biological samples. The samples and the biological targets contained therein can be transported to the imager using a standard microfluidic focusing arrangement defined in a molded upper section of the optofluidic microscope device. The molded upper section of the optofluidic microscope device may define fluid channels, and may comprise a poly-(dimethylsiloxane) (PDMS) material. Electrokinetics or pressure can drive the samples through the fluid channels in the optofluidic microscope device to and through the imager. As the biological targets pass through the imager, the light transmission from the illumination source through each light transmissive region is modulated over time. Using the modulated light signals passing through the light transmissive regions, the image of the targets passing through the imager can be reconstructed.

Figure 1:
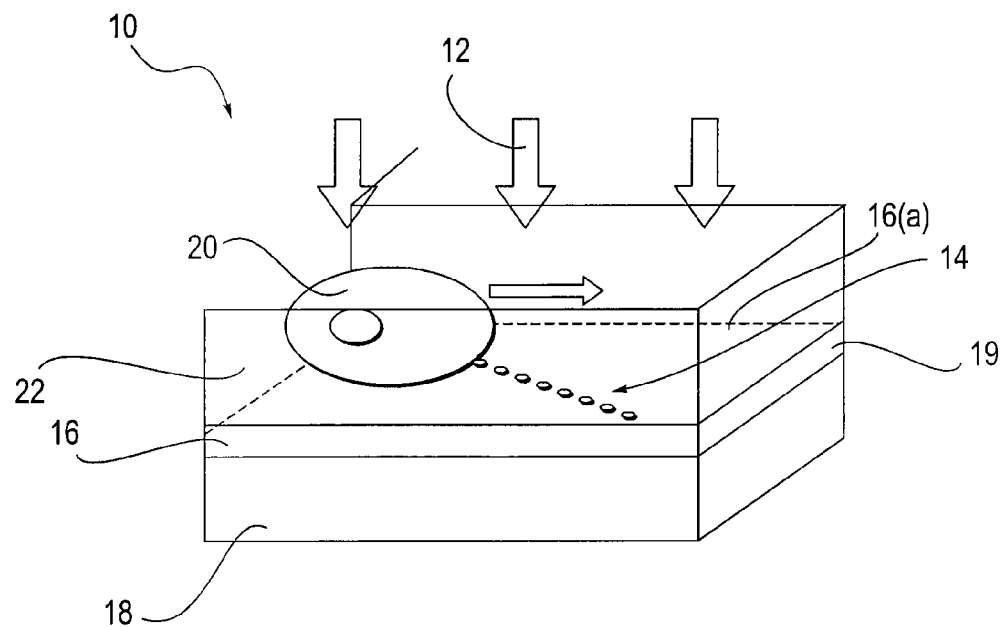
FIG. 1 shows a schematic, perspective drawing of some components of an optofluidic microscope device according to an embodiment of the invention.

FIG. 1 shows a schematic illustration of an optofluidic microscope device 10 according to an embodiment of the invention. The optofluidic microscope device 10 has a body 16, which may be a multilayer structure. It could alternatively be a single, monolithic structure in other embodiments. In the illustrated example, however, the body 16 includes an opaque or semi-opaque layer 19, which in turn has light transmissive regions 14 in it. A transparent protective layer (not shown) may optionally cover the opaque or semi-opaque layer 19 to isolate the opaque or semi-opaque layer 19 from a fluid flowing in a fluid channel 22 in the optofluidic microscope device.

The body 16 may define or include the fluid channel 22 and a surface 16(a) of the body 16 may coincide with the bottom wall of the fluid channel 22. During operation, the fluid channel 22 can have a fluid including a cell 20 flowing in it. Micropumps, electrokinetic devices and other devices (not shown) can be used to cause the fluid to flow through the fluid channel 22.

The fluid channel 22 may have any suitable dimensions. For example, the width and/or height of the fluid channel 22 may each be less than about 10, 5, or 1 micron in some embodiments.

The light transmissive regions 14 in the body 16 are preferably holes. For example, the light transmissive regions 14 may be holes that are etched into a metallic layer such as gold. In the illustrated example, the light transmissive regions 14 form a diagonal line, which extends from one lateral side of the fluid channel 22 to the other lateral side of the fluid channel 22. In other embodiments, the light transmissive regions 14 can be in the form of an array or a one-dimensional line that extends perpendicular to the direction of flow within the fluid channel 22.

An illumination source 12 is on one side of the surface 16(a). Suitable examples of illumination sources include white light sources, natural lighting, colored light sources, etc. The illumination source 12 produces light which passes through the fluid passing through the fluid channel 22. Suitable illumination sources are commercially available.

An optical detector 18 is on the other side of the surface 16(a). The optical detector 18 may include a charge coupled device, and may include an array of discrete light detecting elements that respectively correspond to the light transmissive regions 14. The optical detector 18 could also be a diode array (e.g., a linear or two-dimensional diode array), where each diode in the diode array corresponds to a light transmissive region 14. Suitable optical detectors are also commercially available.

As shown, a fluid including a biological cell 20 may flow through the fluid channel 22. As the cell 20 passes through the fluid channel 22, the light transmissive regions 14 can be used to image the biological cell 20 (or other object). For example, as shown in FIG. 1, a liquid containing a cell 20 may flow through the fluid channel 22. As it flows through the fluid channel 22, light from the illumination source 12 passes through the fluid channel 22 and illuminates the surface 16(a) of the body 16. Light that is not blocked by the cell 20 passes through some of the light transmissive regions 14 substantially unaltered. Light that passes to the cell 20 may be blocked or may be altered in some way (e.g., reduced intensity, altered wavelength, etc.) relative to the light that passes through the cell 20. As noted above, individual light detecting elements (not shown) in the light detector 18 can be respectively associated with the light transmissive regions 14. Each individual light detecting element in the detector 18 is sampled over time and the changes in light received by the light detecting elements over time can be used to image the cell 20. This process is explained in further detail below.

Figure 2:
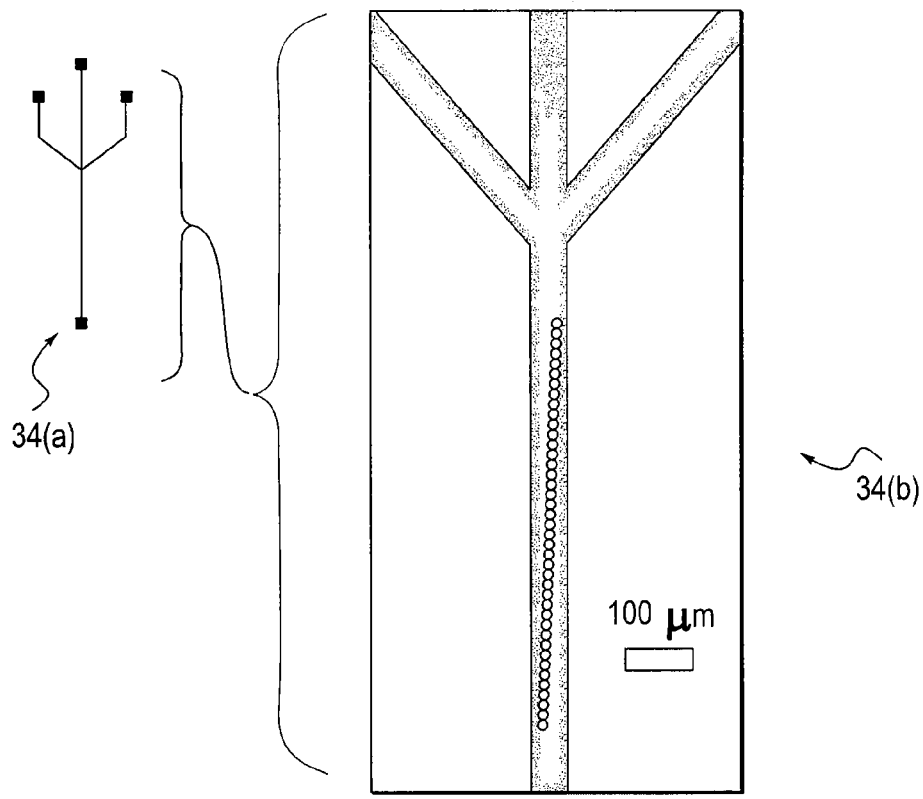
FIG. 2 shows an image of a top view of a working embodiment of an optofluidic microscope device according to an embodiment of the invention. In the image, the width of a fluid channel in the optofluidic microscope device is about 44 microns. A schematic drawing of the fluid channels in the optofluidic microscope device is also shown to the left of the image.

Referring to FIG. 2, reference number 34(*a*) shows a schematic diagram of a microfluidic channel system that can be used in a microfluidic device. Reference number 34(*b*) shows an SEM (scanning electron microscope) image of a portion of the microfluidic channel system corresponding to reference number 34(*a*). As shown by reference number 34(*b*), a line of light transmissive regions extends from one lateral side of a fluid channel to the other lateral side.

The branched fluid channel structure may be used to "focus" a biological target toward the center of the imager including the light transmissive regions. For example, biological targets may flow in the center of the fluid channel of the three upstream fluid channels shown by reference number 34(*a*). The three fluid channels converge into a single fluid channel, the biological targets will stay confined to the center of the single fluid channel. This helps to ensure that the biological target will travel in a substantially straight line as it passes over the light transmissive regions.

The operation of an optofluidic microscope device according to an embodiment of the invention can be further described with respect to FIGS. 3(*a*)-3(*d*). FIG. 3(*a*) is another schematic drawing of an optical device according to embodiment of the invention from a close up view. FIG. 3(*b*) is a top view of the fluid channel in the optical device in FIG. 3(*a*). FIG. 3(*c*) is a side view of the optofluidic microscope device shown in FIG. 3(*a*). FIG. 3(*d*) shows collected time traces from each pixel in the optical device, wherein each pixel can be processed to create an object image.

As shown in FIGS. 3(*a*)-3(*c*), a cell 20 passes through the fluid channel 22 and blocks light transmissive regions 14 as it passes through the fluid channel 22. The cell 20, or other target object, flows through the channel 22 at a constant velocity. Electrokinetic or pressure devices (not shown) can cause the liquid containing the cell 20 to flow so that the cell 20 is confined to the center of the imager. As shown in FIG. 3(*a*), the light transmissive regions 14 are slanted and extend from one lateral side of the fluid channel 22 to the other lateral side of the fluid channel 22. By slanting the light transmissive regions 14, each lateral position of the fluid channel 22 can be monitored and used to image the lateral edges of the cell 20. In other embodiments, the light transmissive regions 14 could be in a straight line that is perpendicular to the walls of the fluid channel 22.

As shown in FIG. 3(*c*), a light detector 18 is under an opaque or semi-opaque layer 19 including a number of light transmissive regions 14. The opaque or semi-opaque layer 19 may be a gold film (which may be present on a transparent layer) and may be, at 100 nanometers, nearly opaque to white light transmission (the skin depth of a 632.8 nanometer He—Ne laser in a gold layer is about 12 nanometers).

Any suitable commercially available light detector may be used in embodiments of the invention. The light detector 18 includes a number of discrete light detecting elements (e.g., pixels) respectively corresponding to the light transmissive regions 14. During operation, the light detector 18 may or may not receive substantially unmodulated light from the illumination source 12 through the light transmissive regions 14. This depends upon whether or not the cell 20 is covering the light transmissive regions 14. Changes in the light signals received through the light transmissive regions 14 over time can be used to image the cell 20.

Illustratively, FIG. 3(*d*) shows collected time traces from each light detecting element under each light transmissive region 14. More specifically, an output for each the light detecting element in the detector 18 over time is shown. Using the known relative positions of the light transmissive regions 14 (and their associated light detecting pixel) and the time traces generated from the discrete light detecting elements in the light detector 18, an object image can be formed as shown in FIG. 3(*d*).

As a target passes over the light transmissive regions 14, the characteristics of the light passing through them are changed in some way. In effect, each light transmissive region 14 functions like a probe tip of a near field optical microscope (NSOM), or as a pinhole in confocal microscope. Embodiments of the invention thus have high sensitivity.

The time trace associated with each light transmissive region is dependent on the profile of the target being imaged as well as its optical properties. For example, a pixel output that corresponds to low intensity at a predetermined position for a predetermined period of time provides data regarding the width of the object at a particular position in the fluid channel. The data for each pixel can be processed using a computer to form an image of the object. In this example, it is presumed that the cell 20 moves in a straight line as it passes through the fluid channel 22 and over the pixels in the detector and over the light transmissive regions 14.

Embodiments of the invention have a number of advantages. Embodiments of the invention provide high resolution, are inexpensive to fabricate, use small sample volumes, are easy to view, and have high throughput. Embodiments of the invention can be as small as a matchbox, are capable of high throughput processing, and are easy to mass produce. As an alternative to conventional bulky microscopes, they are easy and inexpensive to fabricate, and they are compact. Embodiments of the invention can also reach the sub wavelength resolution regime, thus opening up a new field of optical on-chip imaging of small bacteria and viruses. A high throughput approach for imaging and distinguishing different viruses or bacterium types can be important and convenient for biological and clinical usage.

B. Methods for Making the Optofluidic Microscope Devices

The optofluidic microscope devices according to embodiments of the invention can be fabricated in any suitable manner. An exemplary method for fabricating an optofluidic microscope device according to an embodiment of the invention can be described with reference to FIGS. 4(*a*)-4(*e*). Any suitable combination of well known processes including etching, lamination, and soft lithography can be used to fabricate the optofluidic microscope devices according to embodiments of the invention.

Fabrication of the imaging array is shown in FIG. 4(*a*) and begins by first evaporating a layer of gold 34 (approximately 100 nanometers thick) on the transparent surface of a glass plate 32. The glass plate 32 could alternatively be some other transparent layer. The layer of gold 34 could alternatively be any other suitable opaque or semi-opaque layer.

As shown in FIG. 4(*b*), a poly(methylmethacrylate) (PMMA) resist layer 36 is then spun on the gold layer 34 and standard electron-beam lithography used to form a hole pattern in the PMMA resist 36. Instead of a PMMA resist 36, any other suitable type of photoresist may be used.

Figure 4A:
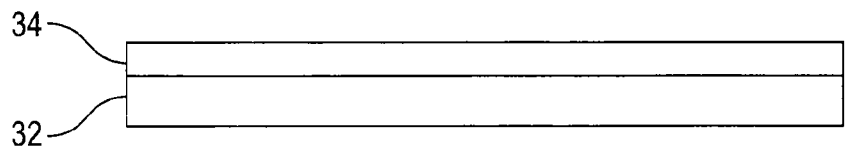
Figure 4B:
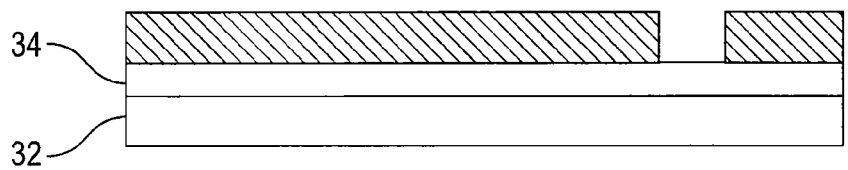
Figure 4C:
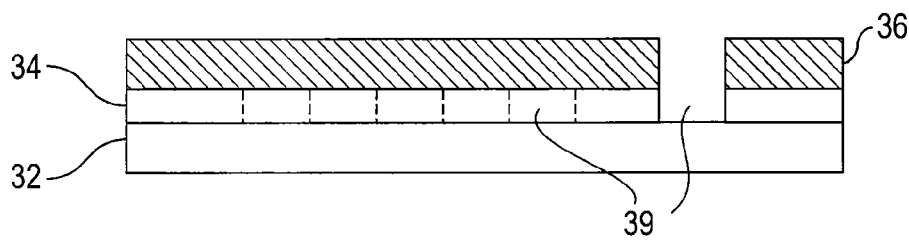

As shown in FIG. 4(c), after developing, the gold layer 34 is wet etched thereby defining the imager holes 39. Alternatively, a dry etching process may be used to form the imager holes 39.

In other embodiments, etching need not be used. For example, a laser ablation process can be used to form the holes 39. In this case, a photoresist layer is not needed to form the holes 39.

Figure 4D:
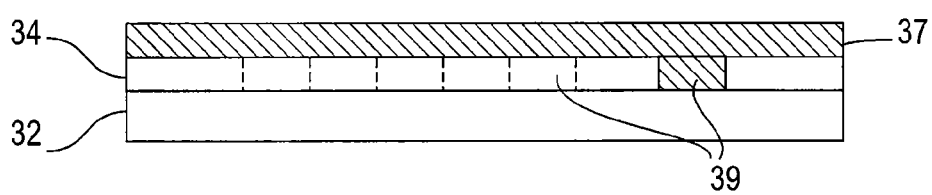

As shown in FIG. 4(d), the remaining PMMA layer 36 is then removed and replaced with a new PMMA film 37 (about 200 nanometers thick) which serves to electrically and mechanically isolate the imager from the fluidics portion of the optofluidic microscope device. Alternatively, instead of a PMMA film 37, a different type of transparent or semi-transparent isolating material can be used.

The new PMMA film 37, the prior PMMA layer 36, and any other layer formed in the optofluidic microscope device may be deposited using any suitable process. Exemplary processes include roller coating, spin coating, vapor deposition, etc.

Figure 4E:
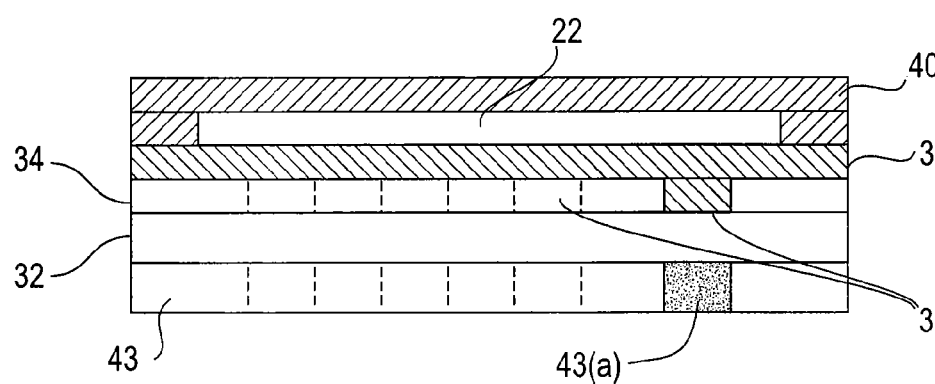

In the final assembly stage, as shown in FIG. 4(e), a PDMS (poly dimethylsiloxane) structure 40 is pre-formed and is then attached to the PMMA film 37. Access holes (not shown) are then punched in the PDMS (poly dimethylsiloxane) structure to form fluid inlets and outlets. The PDMS structure 40 may be formed using a soft lithography technique (well known in the art) and is then exposed to air plasma for about 30 seconds. The PDMS layer 40 and the PMMA film 37 may be laminated together, forming fluid channel 22. After assembly, an 80° C. post bake can be used to help improve bonding strength between the various components of the optofluidic microscope device.

Also, as shown in FIG. 4(e), a detector 43 including discrete light detecting elements 43(a) is then attached to the glass plate 32 using an adhesive or other suitable bonding mechanism to form an optofluidic microscope device according to an embodiment of the invention. As noted above, the light detector 43 may be a commercially available part.

Suitable electronics (not shown) may be connected to the attached detector. Such electronics may comprise a computer comprising image processing software, software for distinguishing between different biological entities, signal processing software and electronics, etc. Those of ordinary skill in the art know what types of electronics can be used in embodiments of the invention to form images from the imager in the optofluidic microscope device. In addition, computer code for performing any of the signal processing or other software related functions may be created by those of ordinary skill in the art. The computer code in any suitable programming language including C, C++, Pascal, etc.

C. Hole Spacing and Resolution

As noted above, in an exemplary optofluidic microscope device, the transmission of light passing through holes in an opaque gold layer is monitored by a detector such as a linear CCD or photodiode array which is directly underneath the opaque layer. This arrangement makes the optofluidic microscope device compact and free of bulk optics. Each hole and the transmission of light through each hole can uniquely map to a single CCD pixel or photodiode. For example, the inter-hole spacing may be on the order of about 13 microns so that the spacing is the same as the spacing of the discrete light detecting elements in a commercially available detector (e.g. a line scan sensor such as a Dalsa tall pixel sensor IL-C6-2048).

The pixel resolution in the y-direction, $r_y$, perpendicular to the flow direction, depends on the spacing of adjacent holes in this direction. The more holes etched through the gold layer per unit width, the higher the achievable resolution as defined by Eq. (1) below, $$r_y = \frac{w}{n_h} \quad (1)$$

where $n_h$ equals to the number of holes and w is the channel width. For example, if the channel width is 40 µm, the y-direction pixel size would be 1 micron if there are 40 holes across the fluid channel. In the x (flow) direction, the pixel size is determined by the acquisition rate of the optical measurement unit and the net velocity of the target (i.e., the resolution in x-direction is equal to target moving speed, u, times the pixel acquisition time Δt) as defined by Eq. (2), $$r_x = u \Delta t, \quad (2)$$

For example, if the target flow speed is 100 microns per second, and the detector's reading rate is 1 KHz, the maximum resolution in the x direction would be equal to about 0.1 micron.

The sensitivity of the optofluidic microscope device depends on the total amount of light transmitted through each hole. Assuming the opaque layer is perfectly conductive, two different regimes of hole size ($S_h$) are examined. They are as follows.

$S_h > \lambda$, Large hole limit—In this regime, the effective transmission area $A_T$ is simply equal to the physical cross section of the hole.

$S_h < \lambda$, Small hole limit—In this regime, assuming that the hole is infinitesimally thin, Bethe (Bethe H A, 'Theory of diffraction by small holes', physics Review, 66, 163 (1944)) showed that the effective transmission area is proportional to the sixth power of the pinhole diameter.

In a recent work, De Abajo (F. de Abajo, 2002, "Light transmission through a single cylindrical hole in a metallic film", Optics Express, vol. 10, pp. 1475-1484) observed that the transmission is further attenuated exponentially as a function of the hole depth. Combining these two effects, the effective transmission area can be expressed as:

$$A_T = \left(\frac{16\pi^3}{27}\right)\left(\frac{S_h^6}{\lambda^4}\right)\exp\left(-4\pi d\sqrt{\frac{0.586^2}{S_h^2} - \frac{1}{\lambda^2}}\right) \quad (3)$$

This formulation agrees well with the simulation data that De Abajo reported. However, for the sake of better estimating optofluidic microscope device performance, the finite conductivity of the material and thus reply on the optics simulation needs to be taken into account. The total transmission photon count for a pixel dwell time τ (also equivalent to the inverse of frame rate) is given by, $$N_T = \frac{\varepsilon I A_T \tau}{h\frac{c}{\lambda}} \quad (4)$$

where $$h\frac{c}{\lambda}$$

is the energy that one single photon carries; I is illumination intensity; and ε is the quantum efficiency of CCD camera.

The dominating noise source includes the photon counting noise (shot noise) and the receiver noise ($n_r\tau$). Thus, the sensitivity can be expressed as:

$$SNR = \frac{N_T}{\sqrt{N_T + (n_r\tau)^2}} \quad (5)$$

Therefore, object imaging with a micron level resolution and 30 dB sensitivity can be readily performed with the use of natural light illumination. In principal, sub-wavelength resolution can be achieved in an optofluidic microscope device by simply spacing the adjacent holes in the y-direction at the desired resolution limit. Since the holes are separated in x-direction by tens of microns, their transmission contributions will be distinguishable from each other on the CCD camera. State of the art nanofabrication technology enables the creation of etching patterns with a resolution within the tens of nanometers. Optofluidic microscope devices with resolutions of below 100 nanometers can be created.

D. Microfluidic Transport of Targets

On the micro and nano scale, fluid flow and particulate transport can be accomplished using numerous different techniques, the most popular of which include traditional pressure driven flow, electrokinetic transport, discrete droplet translocation via electrowetting, or thermocapillarity techniques.

While imaging features created with electron beam lithography can be made as small as 20 nanometers, the ultimate resolution of the optofluidic microscope can be limited by the vertical and horizontal confinement stability of the targets. Physical confinement requires that the channel size be on the order of that of the target being imaged, which for smaller targets (<0.5 micron) could mean channel sizes on the order of hundreds of nanometers.

Electroosmotic transport results from the interaction of an externally applied electric field with an electrical double layer. The electrical double layer is a very thin region of non-zero charge density near the interface (in this case a solid-liquid interface) and is generally the result of surface adsorption of a charged species and the resulting rearrangement of the local free ions in solution so as to maintain overall electroneutrality. As it is a surface driven effect, the electrokinetic velocity is nearly independent of channel size. Therefore, electroosmotic transport is better for the physical confinement and imaging ranges that are ultimately desired.

In addition to physical confinement, fluidic confinement of the targets will be equally desirable for final imaging stability. A number of researchers have studied Brownian particle dynamics and have demonstrated that particles in a shear flow tend to migrate to a particular location where the various hydrodynamic forces acting on the particle equilibrate. For pressure driven flow in low aspect ratio microchannel systems, such as those described here, there exists a strong shear gradient in the vertical direction which will tend to confine the targets at a location roughly 40% of the distance from either the upper or lower surface of the channel to the midpoint (i.e., there are two vertical equilibrium positions). In the horizontal direction, however, there is no significant velocity gradient (i.e., in low aspect ratio channels the parabolic velocity profile in the horizontal direction tends to be very weak) and thus no mechanism to stabilize the targets against Brownian diffusion after it is initially focused into the channel. Recent advancements in localized modification of the electroosmotic mobility in microfluidic devices could allow for velocity profile tuning thereby creating a single shear equilibrium position for confinement against Brownian motion in both the vertical and horizontal directions. Such tuning is difficult to perform with traditional pressure driven flow. Brownian motion effects and ways to address these effects are discussed in further detail below.

An electrokinetic driven microfluidic setup is shown in FIG. 2. As seen in FIG. 2, the fluid from the two side branches acts as a focusing force. The central channel contains the biological targets which are confined to the center of the imager through upstream focusing. By dynamically adjusting the voltage applied to the fluid, biological targets can be driven faster to get into the detection region, but slower when they are passing the detection region for the purpose of obtaining more pixel information. As noted above, the opaque or semi-opaque layer (e.g., perforated gold layer) is isolated from the electrical ports by a thin layer of PMMA. The PMMA layer and the PDMS channels are treated with oxygen plasma for tighter sealing and better flow properties. Embodiments of the invention may use a voltage gradient no higher than 50 V in the target transportation channels and less than 30 V in the focusing channels to drive the biological targets with an appropriate speed for image acquisition.

E. Exemplary Experimental Results

As mentioned above and as illustrated in FIG. 3, with the full information of the transmission time traces, the geometrical profiles of the imaging targets can be reconstructed. A biological target that was imaged was Chlamydomonas provided by Carolina biological supply. Chlamydomonas is a single-celled, biflagellate, green alga. It is roughly circular in shape and has a diameter ranging from about 10-20 microns. It contains several species that have become popular as research tools, because it has well defined genetics that can transformed by well developed techniques. In these initial experiments, an OFM configuration similar to the one shown in FIG. 1 was used. The transmission changes through each hole were recorded by an 8-bit Sony XCD-X710 firewire CCD camera, mounted on Olympus IX-71 inverted microscope.

FIG. 5 shows the transmission change of two adjacent holes when a single Chlamydomonas cell passes over them. Ten continuous picture frames are streamed into a computer program from which the pixel information from each hole is extracted. It can be seen from FIG. 5 that light transmission through holes does respond dynamically to the object flowing across the imaging region. If more frames are rapidly collected, more detailed pixel information can be obtained, and a two dimensional image of a biological sample can be subsequently regenerated.

FIG. 6(a) shows a transmission image of the optofluidic microscope device. The holes are smaller than they appear (0.5 microns). FIGS. 6(b1) and 6(b2) show occlusion time traces through adjacent holes. FIGS. 6(c) shows a microscope image of a chlamoydomonas. FIG. 6(d) shows preliminary data showing an optofluidic microscope device image of a chlamoydomonas.

F. Brownian Motion

The imaging method employed in optofluidic microscope devices assumes that the flow of the target object across the hole array is straight and undeviated during the entire trajectory. Any deviation from a straight trajectory can distort the processed object image.

The achievable image resolution is bounded by the effective deviation of the object along its trajectory. Unintended object trajectory deviations can be caused by temperature gradients, bulk system vibrations, and Brownian motions. While the first two can be minimized by careful system design, there is little that can be done to suppress Brownian motions directly.

The root mean square deviation along a single dimension $$\sqrt{\langle x^2 \rangle},$$

of a spherical particle of diameter l in a fluid of viscosity η on a time scale of t is given by:

$$\sqrt{\langle x^2 \rangle} = \sqrt{\frac{2k_B T}{3\pi \eta l} t} \quad (6)$$

where $k_B$ is the Boltzmann constant and T is the system temperature. An object of diameter 10 microns drifting in room temperature water will experience a mean deviation of 29 nanometers in one dimension for a time period of about 10 milliseconds. There is also a Brownian motion actuated rotation. However, the relative extent of the rotation and its effect on resolution is small compared with the translational Brownian motion deviation effect.

The deviation's inversion dependency on particle size implies that the degrading effect of Brownian motion on the achievable resolution increases with smaller objects. Indeed, an optofluidic microscope device with 30 nanometer resolution and line scan acquisition rate of 10 kHz can be expect to achieve a 100×100 pixel image with image resolution of 70 nanometers when it is used to image a microbe of size 4 microns. It is noted that when high resolution optofluidic microscope devices are used to image relatively large bioentities that are not as pronouncedly impacted by Brownian motion artifacts, the optofluidic microscope devices can easily achieve their predicted resolution.

It is possible to experimentally study and verify a method for correcting motional artifacts attributable to Brownian motions. The method involves building a tracking system into the optofluidic microscope device that is capable of tracking the motional drifts of the target object as it passes through the detection array.

FIG. 7 shows an exemplary embodiment including tracking light transmissive regions. In FIG. 7, tracking sets of light transmissive regions 42 may be interleaved with imaging light transmissive regions 44. In this example, the tracking light transmissive regions 42, each have identical sets of five or six holes and are generally oriented along the center of the fluid channel 22. In comparison, imaging light transmissive regions 44 form of a slanted array of light transmissive regions that extends from one wall of the fluid channel 22 to the other wall of the fluid channel 22. The configuration of the illumination source (not shown) and the detector (not shown) can be as in the previously described embodiments.

Using the tracking light transmissive regions 42, it is possible to track the lateral drift of the object 20 with each tracking set of light transmissive regions 42 as the object flows across the hole array. As the tracking sets are identically placed in the middle of the channel, any signal drift across adjacent set of light transmissive regions 42 can be correlated to the net drift of the object in the y-direction. This drift information can be used to modify any images that are formed using the optofluidic microscope device. The change in the arrival time of the object 20 between tracking sets of light transmissive regions 42 can be correlated to the net drift of the object 20 in the x-direction.

The performance of the optofluidic microscope device can be expected to improve if more tracking sets are used. The resolution uncertainty associated with Brownian motion artifacts should decrease as the square root of the number of tracking set used (assuming the tracking set is regularly spaced). The construction and implementation of optofluidic microscope devices with tracking systems is straightforward.

G. Embodiments Using Light Transmissive Regions and Fluorescence

Some embodiments of the invention use light transmissive regions and fluorescence to image objects. As background for these embodiments, a hole in a thick opaque or semi-opaque conductive layer will effectively transmit only light of wavelength shorter than the cutoff wavelength for zero mode propagation. Light of longer wavelengths is transmitted less efficiently. The approximate formulation of this transmission behavior as a function of the effective transmission area is given by:

$$A_{transmission} = \left(\frac{16\pi^3}{27}\right)\left(\frac{s_h^6}{\lambda^4}\right)\exp\left(-4\pi d \sqrt{\frac{0.586^2}{s_h^2} - \frac{1}{\lambda}}\right). \quad (7)$$

where λ is the wavelength, d is the conductive layer thickness and $S_h$ is the diameter of the hole. This equation is mentioned above. For a sufficiently thick conductive layer, the transmission drops very sharply when λ exceeds $S_h$/.586. If "d" is large, the transmission curve will look like a step function.

The approach for performing simultaneous fluorescence and transmission imaging of the object involves illuminating the sample with the appropriate excitation light field (at wavelength $\lambda_{ex}$). Fluorophores within the sample will absorb and re-emit at a different wavelength $\lambda_f$; $\lambda_f > \lambda_{ex}$. Assuming a uniform illumination field, the transmission at wavelength $\lambda_{ex}$ will project a transmission image of the object, while the fluorescence pattern from the sample projects a fluorescence image of the object. By using both fluorescence and transmission imaging modes, more accurate object images can be produced.

Referring to FIG. 8, it is possible to acquire both images by using an optofluidic microscope device with a pair of interlaced lines of holes 214. The hole size for the first line (or set) of holes 211 can be chosen so that the holes 212 will transmit light of both wavelength $\lambda_f$ and $\lambda_{ex}$. The hole size for the second line of holes 212 will be chosen so that it will only transmit light of wavelength $\lambda_{ex}$. The lines of holes 211, 212 can be arranged such that each pair of holes is at the same lateral displacement from the channel walls, so that they will interrogate the same line across the object. The transmission through the second line of holes 212 can then be used to generate a transmission microscope image of the object flowing through the fluid channel. The fluorescence image of the object can be generated by taking the difference of the transmission through the first line of holes 211 and the second line of holes 212. The configuration of the illumination source (not shown) and the detector (not shown) can be as in the previously described embodiments.

H. Optofluidic Microscope Device Applications

Schematic diagrams of a system using optofluidic microscope devices according to embodiments of the invention is shown in FIGS. 9(a)-9(c). Any of the previously described optofluidic microscope devices can be used in a system such as the one illustrated in FIGS. 9(a)-9(c).

As shown in FIG. 9(a), the system is used as a blood differential unit that is capable of performing blood cell identification and counting. The system includes a number of fluid inlets (e.g., as designated by "sample in" and "reagent in" and fluid outlets (e.g., as designated by "waste out". As shown, there is a mixing changer, and three optofluidic microscope devices in series. The outlets to the optofluidic microscope devices converge into a single recycle stream that is fed back into a "sample" fluid inlet. FIG. 9(b) shows fluids as they pass into the system. FIG. 9(c) shows fluids during operation when fluid is recycled back to a sample in fluid stream.

An exemplary operational procedure is as follows. First, the blood sample of interest and the differential reagent are flowed into a mixing chamber. The differential reagent employed may be varied based on the blood fraction of interest and may include a red blood cell lysing agent, a chemical stain (such as Chlorazole Black), fixing reagent or a diluent. Given the relatively large volume (~1 microliter) of the blood sample and reagent used in this step, the flow may be pressure driven or electrokinetically actuated. Second, the mixture is allowed a sufficient period of time to mix and react (about 10 seconds). Third, the mixture is then driven across the optofluidic microscope devices by electrokinetics. The proposed flow channel will be 20 microns in dimension and each optofluidic microscope device will be designed to have a resolution of 500 nanometers. The optimal flow rate would be about 6.0 millimeters/second.

Each optofluidic microscope device may be fabricated to incorporate a bandpass filter between the device and the associated CCD array. The bandpass filters can provide filtering at 500-550 nm, 550-600 nm, 600-650 nm and 650-700 nm, in order to span a reasonable portion of the visible spectrum. The specifics of the filter may be readjusted based on the spectral components that are of the greatest interest.

In the illustrated embodiment, the expected imaging speed of 1 cell per 1.6 milliseconds. The acquired multi-spectral image data for each cell is processed manually or through an automated program. The processed information can be used to differentiate cells from each other and processed cells may then be channeled to the appropriate collection or disposal reservoir by biasing the correct output voltage at the correct reservoir.

As an additional processing step, any given sorted blood fraction may be reprocessed through the entire system by simply channeling the desired fraction to the input of the system. This fraction may then be mixed with a different differential reagent and imaged and resorted to further distinguish different components in the fraction or simply to collect more information about the fraction as a whole. The ability to reprocess sorted fractions with little or no loss is unique to a microfluidic based cell sorter (a conventional cell cytometry system is generally not designed for reprocessing). This advantage is likely to be a significant factor for future cell sorting applications that use multi-stage processing.

The speed of cell identification and sorting is comparable to that of a commercial blood differential unit (which processes cells at a speed of 1 cell per 200 microseconds). However, the processing speed of embodiments of the invention can be significantly increased by an order of magnitude by simply increasing the number of systems in operation simultaneously on the same chip. Further, embodiments of the invention are more precise and accurate with respect to sorting. In particular, embodiments of the invention can outperform commercial blood differential units in distinguishing between band cells and mature neutrophils, and in the counting of nucleated red blood cells.

The optofluidic microscope device according to embodiments of the invention can potentially be used to identify circulating tumor cells (CTC) in blood. Given that circulating tumor cells (CTC) are generally distinguished and classified based on a visual inspection of their cell or nucleus morphology, an optofluidic microscope based cell sorting system can be used for automated CTC cell counting. The optofluidic microscope device imaging method will be useful in a wide variety of applications, ranging from its incorporation into microfluidic based flow cytometer as an on-chip imaging system, to its use as a high throughput analysis system for the identification and counting of different bacteria types in urine.

II. Optofluidic Devices Using Light Emitting Elements

In conventional optical microscopy, the maximum achievable resolution, as defined by the Rayleigh criterion, is theoretically limited to $\lambda/2$ where $\lambda$ is the optical wavelength of the light involved. (It is also noted that the hole-based method described above will allow for a resolution greater than the $\lambda/2$ limit.) Through the use of novel techniques, such as near field microscopy, entangled photon microscopy, Stimulated Emission Depletion (STED) microscopy, and structured illumination microscopy, it is possible to overcome this limitation to some extent. However, the computational costs, system complexity and optical power requirements rise exponentially as a function of the desired resolution.

Disclosed are other embodiments which can provide images of entities with sub-wavelength resolution in a cost effective manner. These embodiments use a fluorophore array or grid, in which each array or grid point will have a fluorophore that possesses a and distinct fluorescence or Raman emission spectra from the other fluorophores in the array or grid. Suitable fluorophores include quantum dots. Quantum dots can be engineered with distinct, narrow emission spectra and are strong and compact fluorescence emitters. Quantum dots are commercially available and are described in the following exemplary publications: J. K. Jaiswal, H. Mattoussi, J. M. Mauro, S. M. Simon, Long-term multiple color imaging of live cells using quantum dot bioconjugates *Nature Biotechnology* 21, 47 (January 2003); and M. Dahan, T. Laurance, F. Pinaud, D. S. Chemla, A. P. Alivisatos, M. Sauer, S. Weiss, Time-gated biological imaging by use of colloidal quantum dots *Optics Letters* 26, 825 (2001)). While embodiments of the invention are described using quantum dots, embodiments of the invention are not limited to quantum dots.

There are a number of potential applications for the embodiments of the invention that use light producing elements. For example, embodiments of the invention can be used as a means to profile bacteria or virus shape as a way to identify their species, as a means to profile a large protein shape, as a means to measure and obtain the shape of a cell nucleus as a way to identify cancerous cells, a means to measure the refractive index profile of a cell, and as a means to identify the shape of small objects for quality control or other purposes in manufacturing, synthesis and production.

An exemplary optofluidic microscope device including light emitting elements is shown in FIG. 10(a). In FIG. 10(a), a grid of quantum dots 62 is embedded in or present on a surface 16(a) of a body. Each quantum dot 62 has a distinct fluorescence emission spectrum from those of the other quantum dots 62. As shown in FIG. 10(a), an object 20 is on the grid of quantum dots 62 and is imaged using the quantum dots 62.

The quantum dots 62 may have sizes on the order of about 10 nanometers, and the spacing between adjacent quantum dots can be as small as 10 nanometers. Other grid spacing and other sizes of quantum dots can be used in other embodiments of the invention.

To image the shape and size of an object 20, the object 20 is placed on top of the grid of quantum dots 62 and is subjected a uniform illumination field from an illumination source (not shown). Quantum dots 62 that are under the object 20 will receive less illumination and will therefore fluoresce less.

By collecting the fluorescence from the entire grid and spectrally resolving the spectrum with the use of a commercially available spectrometer (or other detector), it is possible to determine which quantum dots 62 are covered. For example, the positions of the quantum dots 62 and the respective fluorescent emission spectra associated with quantum dots 62 are known. Using a spectrometer, a computer can determine which fluorescent spectra have been received by the spectrometer and can consequently determine which specific grid points are covered by the object 20. From this, the shape of the object 20 can be derived with a resolution that is limited only by spacing of the quantum dots 62.

Instead of composing a grid of quantum dots, an alternate configuration for the microscope can be one where a linear array of distinct quantum dots 62 is employed. The quantum dots 62 are on or under the surface 16(a). This is shown in FIG. 10(b). In FIG. 10(b), distinct quantum dots 62 are disposed in a line that runs perpendicular to the direction of the flow of the object 20. As in the previously described embodiments, it is possible to measure the fluorescence spectra of the quantum dots 62 over time to determine which the quantum dots 62 are covered. In this example, the object 20 flows across the array of quantum dots 62 through a fluid channel 22. The time changing fluorescence spectrum can then be processed to provide sufficient data to determine the shape of the object 20.

The arrangement of the detector and the illumination source in the optofluidic microscope device embodiments shown in FIGS. 10(a) and 10(b) can vary. Two exemplary configurations are shown in FIGS. 11(a) and 11(b). FIGS. 11(a) and 11(b) are side schematic views of embodiments of the invention. In FIGS. 11(a) and 11(b), like numerals designate like elements.

In FIG. 11(a), an illumination source 420 may provide light of a predetermined first wavelength. The light of a first wavelength 430 may excite a quantum dot 62 disposed on or within the body 410(a) so that light of a second wavelength 431 is provided by the quantum dot 62. The light of the second wavelength 431 may be received by the detector 432. When the cell 20 passes over the quantum dot 62, it blocks or modulates the light of the first wavelength 430 so that the light emitted from the quantum dot 62 is different than the light of the second wavelength 431 that was previously received by the detector 432. In this example, the body 410(a) may be transparent, semi-transparent, or opaque, since the illumination source 420 and the optical detector 432 are above the quantum dot 62 and the body 410(a).

FIG. 11(b) shows another embodiment with a different configuration. In this embodiment, the detector 432 is under the body 410(b). In this embodiment, the body 410(b) is transparent or semi-transparent so that the light of the second wavelength 431 can pass through it to the detector 432.

In yet other embodiments, if the bodies 410(a), 410(b) are transparent or semi-transparent, transparent the illumination source 420 could alternatively be on the under the bodies 410(a), 410(b). The detector 432 could be positioned over or under the bodies 410(a), 410(b).

An alternate microscope having a microfluidic channel can be fabricated. This is shown in FIG. 12. The quantum dots 62 are laid down in two or more sets 64 of lines 62(a) on the substrate 22. Each line 62(a) has the same distinct quantum dots 62, and each line will have a different emission spectrum from the other lines 62(a). The orientation of each set 64 can be different. In the embodiment shown in FIG. 14, the fluorescence spectrum can be measured to determine occlusion still applies. In this case, the extent of fluorescence diminishment in a specific spectral band is an indication of the extent to which a specific line of quantum dots is covered by the object.

After making a measurement using a set of lines, the object 20 flows to the next set 64 of quantum dot lines. The transport is performed in a manner that the orientation of the object 20 is unperturbed. The process is repeated for all line sets 64. By performing computed tomography computations on the line sets 64, one can determine the shape of the object 20.

The configuration in FIG. 12 has advantages over the previous configurations. For example, the shape of the object 20 on an N×N grid can be found with the use of N distinct types of quantum dots. In the prior embodiments described above, the same resolution requires the use of $N^2$ distinct types of quantum dots.

Referring to FIGS. 13 and 14, if the object is too transparent and does not occlude a sufficient amount of the excitation light field from the quantum dots to sufficiently diminish the emission from the quantum dots, embodiments of the invention can instead rely on the use of an evanescent excitation field.

The excitation light field 70 is directed toward the quantum dots 62 on or under the surface 16(a) of the fluid channel 22 in a body. It is carefully adjusted such that its angle of incidence on the glass-channel interface is over the critical angle. In this situation, aside from an exponentially decaying evanescent field, very little of the optical excitation field will reach the quantum dots 62 and the quantum dots 62 will not fluoresce or fluoresce very weakly. If an object 20 with a higher refractive index than the liquid medium flowing in the channel were to cross the path of the excitation light field 70, it will see a change in the refractive index.

As shown more clearly in FIG. 14, if the new refractive index formed by the presence of the object 20 is sufficiently high enough to change the critical angle to a larger value, then the optical excitation field will now become a propagating field 82 in the fluid channel 22. The propagating field 82 can thereafter excite the quantum dot 88 under the object 20 and an imaging system 122 (which may include an optical filter) and detector 124 can receive the light produced by the quantum dot 88. In these embodiments, a fluorescence signal from a particular array grid point indicates that a particular quantum dot 88 at that grid point is occluded.

The optofluidic microscope device embodiments described with reference to FIGS. 13 and 14 can be used for other purposes. For example, they can be used to interrogate the object's 20 refractive index profile. By changing the angle of incidence of the excitation light field and determining when the transmission becomes a propagating wave through the object 20, one can accurately measure its refractive index profile.

FIG. 15 shows yet another optofluidic microscope device according to an embodiment of the invention. The embodiments used quantum dots that were laid down in a staged line pattern 106. The difference in fluorescence signal associated with adjacent lines 104 could be attributed to a specific location on the object.

An optofluidic microscope device like the one shown in FIG. 15 can also be implemented with slits (not shown) instead of lines of quantum dots. If the slits are sufficiently narrow and they are illuminated from the bottom, an evanescent field will be set up on the top of the substrate. The flow of an object over a given slit region will turn the evanescent wave to a propagating one. By measuring the total transmission, one can determine a similar set of information as that obtained using the described quantum dot approach.

The optofluidic microscope devices including light emitting elements can be made in any suitable manner. In one example, to create the microscope configuration shown in FIG. 15, a photolithography and etching process can be used to etch out the requisite lines in a body (e.g., a substrate). Each conductive line can then be selectively charged, and a solution containing non-distinct quantum dots that are oppositely charged can be made to attach to the chosen line by flowing the quantum dots across the lines. The adhesion of the quantum dots to the charged line can then be made permanent by coating over the adhered substrate. The process can then be repeated with a different conductive line and a different set of non-distinct quantum dots until the complete line sets are completed. The resolution of the quantum dot array grid is only limited by the achievable lithography etching resolution.

In another approach, a fine needle tip actuator system may be used. In this approach, the creation of a single grid point uses a mixture of quantum dots and a carrier such as an epoxy. The deployed needle tip will then be dipped into the mixture and moved onto the right location on the substrate to deposit a single drop of the mixture. The process will then be repeated for different quantum dots-epoxy mixture until the entire grid is completed. The resolution of the quantum dot grid is only limited by the achievable fidelity of the needle tip to move to a specific location.

Quantum dots can be made with emission linewidths of about 10 nanometers. If one assumes that the accessible emission spectrum that one can observe the fluorescence is about 300 nanometers, this will imply that it is possible to distinctively detect 30 different types of quantum dots. In this situation, the grid dimension proposed in the microscope configuration shown in FIG. 10 cannot be larger than 5×5. Larger grid sizes can be achieved if different spectrometers are dedicated to different sub-sections of the grid. In this scenario, the highest grid density is given by equating the 5×5 subgrid to an area of (½ wavelength)×(½ wavelength). A tighter grid arrangement cannot be adequately resolved by the collection optics of the spectrometer. This, in turn, implies that the resolution achievable by this microscope configuration is about 100 nanometers.

Lastly, the achievable resolution can be a direct function of the number of distinct quantum dot types that are available. As such, it is highly desirable to tailor quantum dots with even narrower emission bandwidth. As an alternative to this, fluorescence resonance energy transfer spectroscopy (or some associated phenomena) could be used. For example, dye pairs can be fabricated whereby one component of the dye pair absorbs light, while the other emits light. The absorptive component can be engineered to have a narrow absorption bandwidth and the emittive component a narrow emittive component. By different permutative combinations of these dye pairs with distinct absorptive and emittive wavelengths, it is possible to create a much larger number of non-degenerate dye types.

III. Other Optofluidic Device Embodiments

FIG. 16 shows yet another optofluidic microscope device embodiment. In this embodiment, the substrate 22 is embedded with an angled linear array of distinct quantum dots or nanoparticles. The horizontal separation between the quantum dots 88, distance u 112, is arranged to be sufficiently large so that it is possible to resolve two distinct dots from each other when the arrangement is imaged onto a CCD camera or other imaging device. Distance u can be equal or larger than the pixel size of the CCD camera if one is performing one-to-one imaging. Distance v 110 sets the resolution of this microscope and can therefore be as small as possible. Ideally, it is equal to the size of the nanoparticles involved.

The object 20 flows through the fluid channel 22 and the fluorescence spectrum from each quantum dot 88 is monitored on an imaging CCD camera (not shown). The CCD camera can be mounted underneath the surface 16($a$) if the surface 16($a$) forms part of a transparent body. Otherwise, it is possible to image the object 20 from above. However, this requires some degree of care in ensuring that the total internal reflected light from the original input beam isn't detected by the CCD. As the quantum dots 88 are sufficiently spaced apart, each quantum dot 88 will be distinctly associated with a pixel on the CCD. Assuming that the shape of the object 20 is unchanged in its transition across the quantum dots 88, it is possible to determine its shape from time traces of the CCD signals.

Whereas the previous microscopy configuration can be thought of as approaches for spectrally encoding sub-wavelength spatial information, this method can be interpreted as an approach for spatially encoding sub-wavelength spatial information into above-wavelength spatial information.

There are two distinct advantages associated with this approach. First, the fluorophores do not have to be distinct. The entire array of quantum dots can be non-distinct. This simplifies the fabrication procedure for the device. There is no need for distinct quantum dots. Eliminating the requirement of distinct quantum dots allows for the use of other contrast mechanisms. One contrast mechanism may involve the use of nanoparticles. Nanoparticles have enhanced scattering cross-sections compared to their physical cross-sections. If they are used in place of the quantum dots, their scattering signals can be used in place of fluorescence signals generated from the quantum dots.

As a rough calculation, if one wants a resolution of 10 nanometers and the object is one micron in dimension, a microfluidic channel that is at least 1 millimeter long (assumes one-to-one imaging onto a 10 micron pixel size CCD, u=10 micron, v=10 nanometers) can be used.

Referring to FIG. 17, another configuration is shown. This configuration is similar to some of the above-described embodiments. Instead of embedding individual quantum dots in a spaced grid, it is possible to lay down a line of quantum dots 160 in the bottom surface 16(a) of a fluid channel 22. The line of quantum dots 160 can have different segments 152, 154 that map onto discrete light detecting elements in a detector (not shown).

The embodiment in FIG. 17 can be formed by creating a trench in a body and then depositing quantum dots into the trench. As long as each segment of the quantum dot line maps to a single pixel on the CCD, the resolving capability of this embodiment is comparable to the previous embodiments. It is also noted that light-scattering nanoparticles can be used in place of the quantum dots in other embodiments.

The embodiment shown in FIG. 17 has advantages. First, compared to prior embodiments, there is a much larger signal due to the larger number of fluorophores or quantum dots contributing to the signal. Second, the embodiment shown in FIG. 17 is easy to fabricate. Embedding a line of fluorophores should be easier than laying down regularly spaced fluorophores.

FIG. 18 shows a configuration is another variant of the configuration in FIG. 17. In this case, a transmissive or reflective line 178 across the body of the optofluidic microscope device. The reflected or transmitted signal is imaged in a similar fashion onto a CCD or other detector. Different segments 174, 176 of the line 178 may correspond to discrete light detecting elements in a detector that may be under the surface 16(a) forming the fluid channel 22. The processing of the signals from the detector to determine the shape of the object 20 is the same as in the previously described embodiments. This embodiment is easy to fabricate.

Yet other embodiments are also possible. For example, it is possible to use a set of periodically textured bull's eye ring patterned transmissive holes, such as those described in H. J. Lezec, A. Degiron, E. Davaux, R. A. Linke, L. Martin-Moreno, F. J. Garcia-Vidal, T. W. Ebbesen, Beaming Light from a Subwavelength Aperture *Science* 297, 820 (2002). An appropriately designed patterned hole will be able to transmit light efficiently with a small divergence angle. The well confined light transmission can dramatically cut down on any blurring artifact during the transmission process.

Yet other embodiments of the invention can use light transmissive regions with different sizes. Using such light transmissive regions, it is possible to determine the shape of an object passing over the light transmissive regions using a light transmission spectrum.

FIG. 19 shows a graph of light transmission vs. wavelength for a single light transmissive region or hole. In this situation, a hole in a thick enough conductive layer can transmit only light of wavelength shorter than the cutoff wavelength for zero mode propagation. That is, a hole of a particular size will pass light of a specific range of wavelengths, while a hole of another size will pass light of a different range of wavelengths.

Other embodiments of the invention can be described with respect to FIGS. 20(a)-20(d). As shown in FIG. 20(a), a body 702 comprises a plurality of light transmissive regions (e.g., holes) 704 with different dimensions. In this example, the light transmissive regions are in an array and each of the light transmissive regions in the array has a different size. The array in FIG. 20(a) has nine holes labeled 704(a)-704(i), each hole having a different size. The holes have circular, radial cross-sections, and may have any suitable depth. In other embodiments, the holes can have rectangular or square cross-sections if desired. It is also possible to have holes with different cross-sectional shapes within an array.

As shown in FIG. 20(b), a portion a-i of the transmission spectrum in FIG. 20(b) may be respectively associated with each hole 704(a)-704(i). As shown in FIG. 20(a), hole 704(a) is the largest hole in the array and corresponds to a portion a spectrum in FIG. 20(b) and allows transmission of light with the greatest range of wavelengths and also has the lowest transmission of light. In comparison, hole 704(i) is the smallest hole in the array and corresponds to a portion i of the spectrum in FIG. 20(a) and has the highest transmission of light.

Stated differently, the height of each step in FIG. 20(b) can correspond to the transmission through a specific hole. By monitoring the transmission spectrum, it is possible to derive the occlusion pattern of an object that is on the array. Within an array, there can be at least about 2, 5, or even at least 10 distinct hole types and/or sizes (assuming a fabrication tolerance of about 10 nm).

As shown in FIG. 20(a), the sizes of the holes in an array may increase or decrease in an orderly fashion within a row or column. Such order can help to produce transmission spectra that can more easily represent an object passing over the array of holes. Preferably, the array of holes is two-dimensional and the sizes of the holes increase within rows and/or columns. As shown in FIG. 20(a), the increase in size can be from one end of a row (or column) to the other end. Successive rows (or columns) can then have increasingly bigger holes.

As shown in FIG. 20(c), an object 700 (e.g., a cell) passing over the array of holes 704 blocks holes 704(b), 704(c), and 704(f). As shown in FIG. 20(d), the portions b, c, and f of the spectrum (see FIG. 20(b)) associated with holes 704(b), 704(c), and 704(f) are not present. Using the spectra in FIGS. 20(a) and 20(c) and knowing the spatial locations of the differently sized holes 704(a)-704(i), it is possible to determine the shape of the object 700 passing over the array of holes 704.

It is preferable to create holes with as small a diameter as possible, so that the density of holes in the body may be increased (and thereby increasing the resolution). Circular holes and holes of any arbitrary shape may be used in embodiments of the invention. The transmission may also be increased by filling the holes with a high refractive index material. This effectively decreases the effective wavelength within each hole and allow for the existence of more propagative modes or a zero-mode waveguide with a decay factor that is small. High transmission is desirable as it enhances the sensitivity of the system and allows easier measurements of the transmission.

FIG. 21 shows a schematic diagram of a system according to an embodiment of the invention. FIG. 21 shows a patterned hole array (previously described) 800 which receives light from a light source 790. An object 806 passes over the hole array and blocks specific holes in the array 800. Light passing through the array 800 passes to a microscope 810 with a CCD camera 804. A computer (not shown) may be operatively coupled to the CCD camera 804 and may comprise a processor, and a computer readable medium with code for determining which pixels in the CCD camera 804 receive light, code for analyzing a transmission spectrum produced using the array of holes 800 and the CCD camera 804, and code for using the transmission spectrum to image and/or analyze the object 806 passing over the array 800.

In embodiments of the invention, it is possible to map a location on the body of area $A_{pixel}$ (limited by microscope resolution) onto a single pixel on an imaging camera such as a CCD device. It is possible to fill each area $A_{pixel}$ with a set pattern of 10 distinct holes. If one measures the transmission spectrum from each hole, embodiments of the invention can achieve a resolution with pixel sizes 10 times smaller than $A_{pixel}$. In other words, if an original imaging system has a resolution of X microns, this approach enhances the resolution to be sqrt(N)X microns, where N is the number of distinct holes.

The simplest approach for obtaining the spectral transmission profile may be to simply scan the input light wavelength and acquire multiple images with the camera.

It is understood that the embodiments of the invention described with reference to FIGS. 20(a)-20(d), and 21 can be combined with the features of any of the previously described embodiments without departing from the scope of the invention. For example, the fabrication methods, materials, dimensions, and systems specifically described with respect to FIGS. 1-9 can be combined with the details of the embodiments described with respect to FIGS. 20(a)-20(d) without departing from the scope of the invention.

The embodiments shown in FIGS. 20(a)-20(d), and 21 have advantages over the previously described embodiments. A first advantage is that this results in a more compact system. A second advantage is that the imaging of the object is done in 1 shot and the time frame is limited by the camera frame rate. In the case where a scanning wavelength light source is used, it is limited by the time it takes for the source to scan a cycle. Movements of the object between imaging frames will not degrade image quality.

The terms and expressions which have been employed herein are used as terms of description and not of limitation, and there is no intention in the use of such terms and expressions of excluding equivalents of the features shown and described, or portions thereof, it being recognized that various modifications are possible within the scope of the invention claimed.

Moreover, one or more features of one or more embodiments of the invention may be combined with one or more features of other embodiments of the invention without departing from the scope of the invention.

All patents, patent applications, publications, and descriptions mentioned above are herein incorporated by reference in their entirety for all purposes. None is admitted to be prior art.

A recitation of "a", "an" or "the" is intended to mean "one or more" unless specifically indicated to the contrary.

What is claimed is:

1. An optofluidic microscope device comprising:
a body comprising a fluid channel having a surface and configured to flow a fluid and an object in a flow direction;
a plurality of light transmissive regions in the body, wherein at least two of the plurality of the light transmissive regions have different dimensions for passing light of different ranges of wavelengths;
an illumination source providing illumination through the light transmissive regions; and
an optical detector receiving light from the illumination source through the light transmissive regions;
wherein the light transmissive regions are located between the optical detector and the object being imaged by the optofluidic microscope device.

2. The optofluidic microscope device of claim 1 wherein the surface is the bottom of the fluid channel.

3. The optofluidic microscope device of claim 1 wherein the light transmissive regions are holes, and wherein the different dimensions are different diameters.

4. The optofluidic microscope device of claim 1 wherein the optical detector comprises a charge coupled device.

5. The optofluidic microscope device of claim 1 wherein the optical detector includes a plurality of discrete light detecting elements, wherein the light detecting elements respectively correspond to the light transmissive regions.

6. The optofluidic microscope device of claim 1 wherein the fluid channel has a bottom with a width of less than about 1 micron.

7. The optofluidic microscope device of claim 1 wherein the light transmissive regions comprise an optically transparent material.

8. The optofluidic microscope device of claim 1 wherein the light transmissive regions form an array of holes that extends from a first side of the surface to a second side of the surface.

9. The optofluidic microscope device of claim 8 wherein the first and second sides are substantially parallel to the flow direction through the fluid channel.

10. The optofluidic microscope device of claim 1 wherein the surface is part of a bottom wall, and wherein the optical detector is attached to the bottom wall.

11. The optofluidic microscope device of claim 1 wherein the light transmissive regions form a slanted line.

12. The optofluidic microscope device of claim 11 wherein the slanted line extends from a first side to a second side of the fluid channel, the first and second sides substantially parallel to the flow direction through the fluid channel.

13. The optofluidic microscope device of claim 1 wherein the illumination source provides white light.

14. The optofluidic microscope device of claim 1 wherein the body comprises a polymeric material.

15. A method of using the optofluidic microscope device of claim 1, wherein the method comprises:
flowing the fluid comprising the object through the fluid channel.

16. The method of claim 15 wherein the light transmissive regions have circular radial cross-sections.

17. The method of claim 16 wherein the light transmissive regions comprise holes.

18. The method of claim 16 wherein the light transmissive regions are holes with a high index of refraction material in the holes.

19. The method of claim 15 wherein the object is a cell.

20. The method of claim 15 further comprising:
detecting a transmission spectrum of the light passing through the light transmissive regions.

21. The method of claim 20 further comprising:
imaging the object using the transmission spectrum.

22. The optofluidic microscope device of claim 1, further comprising a set of three upstream channels that converge into the fluid channel for positioning the object being imaged through the fluid channel.

23. The optofluidic microscope device of claim 1, wherein the light transmissive regions form a two-dimensional patterned hole array.

* * * * *